(12) United States Patent
Mihardja et al.

(10) Patent No.: US 9,907,856 B2
(45) Date of Patent: Mar. 6, 2018

(54) CARBOXYMETHYLCELLULOSE-PEPTIDE CONJUGATES AND METHODS FOR USING THE SAME

(71) Applicant: The Regents of the University of California, Oakland, CA (US)

(72) Inventors: Shirley Sulastri Mihardja, Daly City, CA (US); Jose Antonio Gonzales, Kingsville, TX (US); Randall J. Lee, Hillsborough, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/903,231

(22) PCT Filed: Jul. 2, 2014

(86) PCT No.: PCT/US2014/045303
§ 371 (c)(1),
(2) Date: Jan. 6, 2016

(87) PCT Pub. No.: WO2015/006141
PCT Pub. Date: Jan. 15, 2015

(65) Prior Publication Data
US 2016/0144044 A1 May 26, 2016

Related U.S. Application Data

(60) Provisional application No. 61/843,789, filed on Jul. 8, 2013.

(51) Int. Cl.
| | | |
|---|---|---|
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *A61K 47/48* | (2006.01) |
| *A61K 38/39* | (2006.01) |
| *A61K 9/00* | (2006.01) |
| *A61K 47/38* | (2006.01) |
| *A61K 47/61* | (2017.01) |

(52) U.S. Cl.
CPC ........ *A61K 47/4823* (2013.01); *A61K 9/0019* (2013.01); *A61K 38/39* (2013.01); *A61K 47/38* (2013.01); *A61K 47/61* (2017.08)

(58) Field of Classification Search
CPC .. A61K 38/39; A61K 47/4823; A61K 9/0019; A61K 47/38
See application file for complete search history.

(56) References Cited

U.S. PATENT DOCUMENTS

| | | | |
|---|---|---|---|
| 5,722,403 | A | 3/1998 | McGee et al. |
| 5,797,903 | A | 8/1998 | Swanson et al. |
| 5,885,278 | A | 3/1999 | Fleischman |
| 5,938,660 | A | 8/1999 | Swartz et al. |
| 5,971,983 | A | 10/1999 | Lesh |
| 6,012,457 | A | 1/2000 | Lesh |
| 6,024,740 | A | 2/2000 | Lesh et al. |
| 6,071,279 | A | 6/2000 | Whayne et al. |
| 6,117,101 | A | 9/2000 | Diederich et al. |
| 6,164,283 | A | 12/2000 | Lesh |
| 6,214,002 | B1 | 4/2001 | Fleischman et al. |
| 6,241,754 | B1 | 6/2001 | Swanson et al. |
| 6,245,064 | B1 | 6/2001 | Lesh et al. |
| 6,254,599 | B1 | 7/2001 | Lesh et al. |
| 6,305,378 | B1 | 10/2001 | Lesh |
| 6,371,955 | B1 | 4/2002 | Fuimaono et al. |
| 6,383,151 | B1 | 5/2002 | Diederich et al. |
| 6,416,511 | B1 | 7/2002 | Lesh et al. |
| 6,471,697 | B1 | 10/2002 | Lesh |
| 6,500,174 | B1 | 12/2002 | Maguire et al. |
| 6,502,576 | B1 | 1/2003 | Lesh |
| 6,514,249 | B1 | 2/2003 | Maguire et al. |
| 6,522,930 | B1 | 2/2003 | Schaer et al. |
| 6,527,769 | B2 | 3/2003 | Langberg et al. |
| 6,547,788 | B1 | 4/2003 | Maguire et al. |
| 8,889,140 | B2 * | 11/2014 | Lee ............... A61K 47/48415 424/178.1 |
| 9,610,357 | B2 * | 4/2017 | Yayon ............... A61K 47/4823 |
| 2005/0271631 | A1 | 12/2005 | Lee et al. |
| 2008/0065046 | A1 | 3/2008 | Sabbah et al. |
| 2008/0065047 | A1 | 3/2008 | Sabbah et al. |

(Continued)

FOREIGN PATENT DOCUMENTS

WO    2011163492    12/2011

OTHER PUBLICATIONS

Jyotsna et al. Carbodiimide Used in Coupling Triiodothyronine Antibody to Carboxymethyl-Cellulose Powder for Solid-Phase Radioimmunoassay. Clinical Chemistry, 1986. vol. 32, No. 1, p. 229.*
Reeves et al. Synthesis and Characterization of Carboxymethylcellulose-Methacrylate Hydrogel Cell Scaffolds. Polymers, 2010. vol. 2, pp. 252-264. (Year: 2010).*
Rowley et al. (1999) "Alginate hydrogels as synthetic extracellular matrix materials," Biomaterials 20(1):45-53.
Ogushi et al. (2007) "Synthesis of Enzymatically-Gellable Carboxymethylcellulose for Biomedical Applications," 104(1):30-33.

(Continued)

*Primary Examiner* — Marcela M Cordero Garcia
(74) *Attorney, Agent, or Firm* — Rudy J. Ng; Carol L. Francis; Bozicevic, Field & Francis LLP

(57) ABSTRACT

Provided are compositions for repairing an injured tissue. The composition includes carboxymethylcellulose conjugated to an extracellular matrix derived peptide, and a methylcellulose. Also provided are kits and methods for using the subject compositions.

19 Claims, 9 Drawing Sheets

(56) References Cited

U.S. PATENT DOCUMENTS

| | | |
|---|---|---|
| 2008/0069801 A1 | 3/2008 | Lee et al. |
| 2008/0249026 A1 | 10/2008 | Roberts et al. |
| 2010/0291060 A1 | 11/2010 | Sturk et al. |
| 2010/0291080 A1 | 11/2010 | Lee et al. |
| 2011/0045044 A1* | 2/2011 | Masinaei ............ A61L 27/3604 424/422 |
| 2011/0046038 A1 | 2/2011 | Healy |
| 2013/0123462 A1 | 5/2013 | Dimarchi et al. |

OTHER PUBLICATIONS

Mochizuki et al. (2007) "Integrin-Dependent Cell Behavior on ECM Peptide-Conjugated Chitosan Membranes," Peptide Science,88 (2):122-130.

* cited by examiner

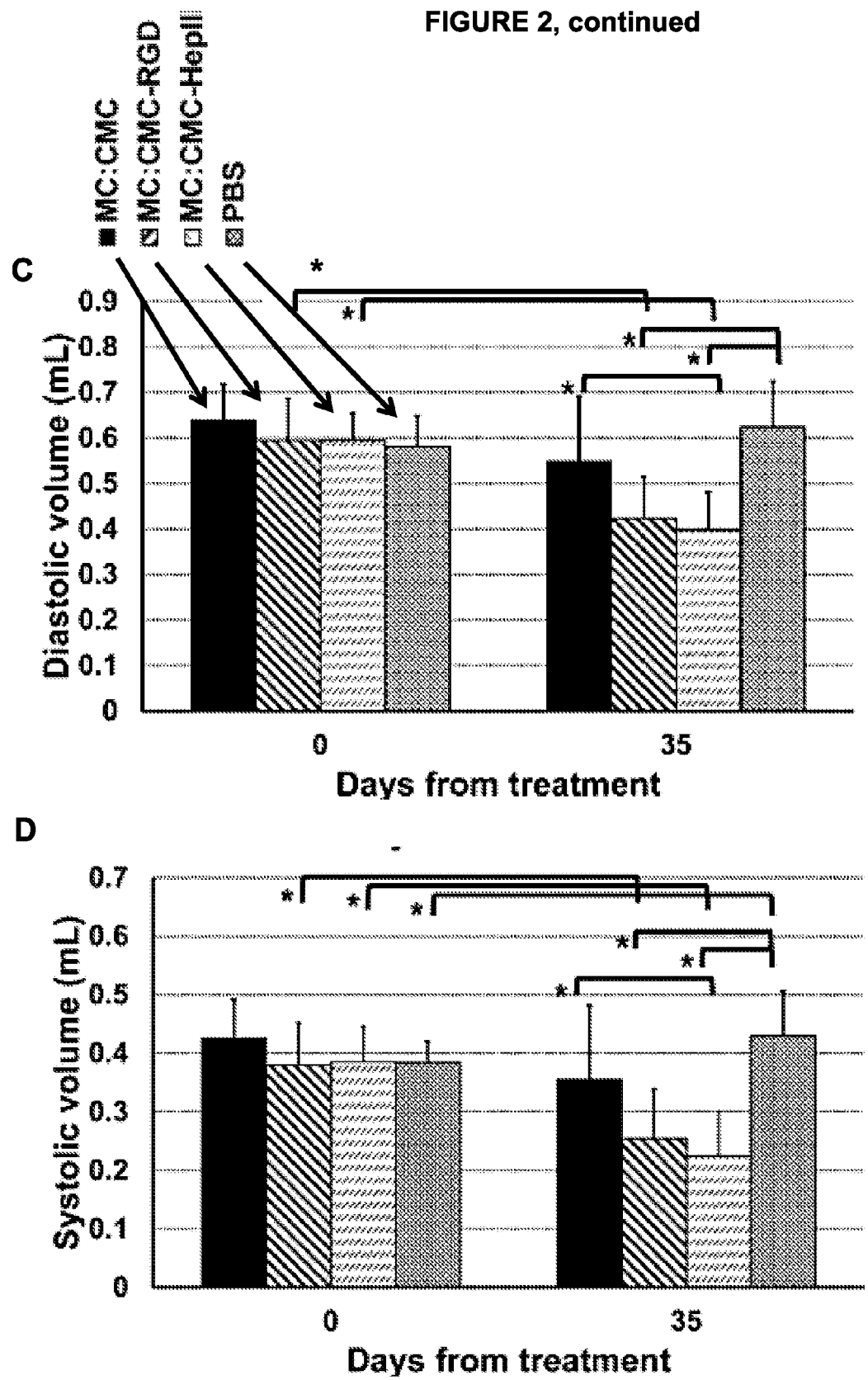

Figure 2:
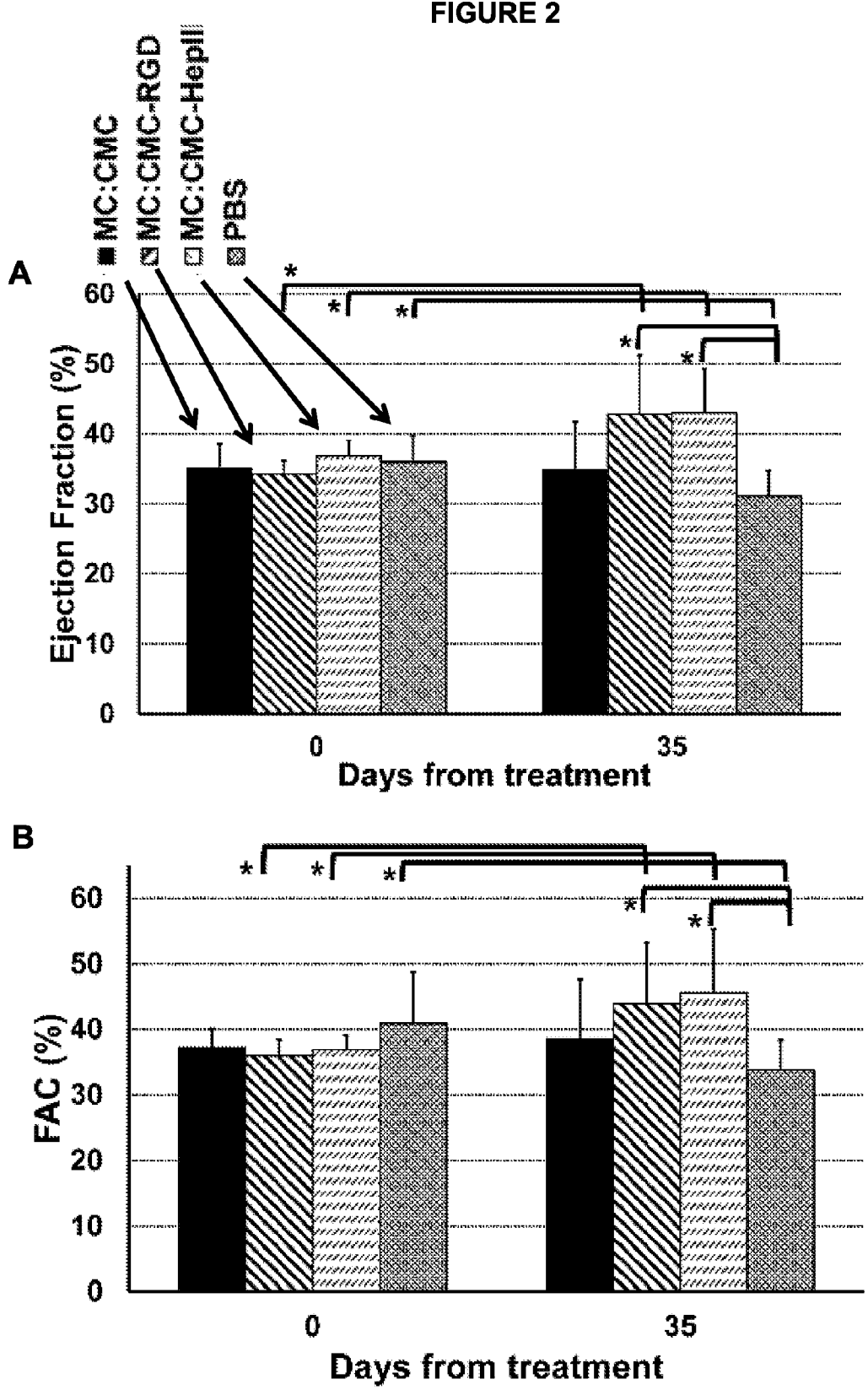

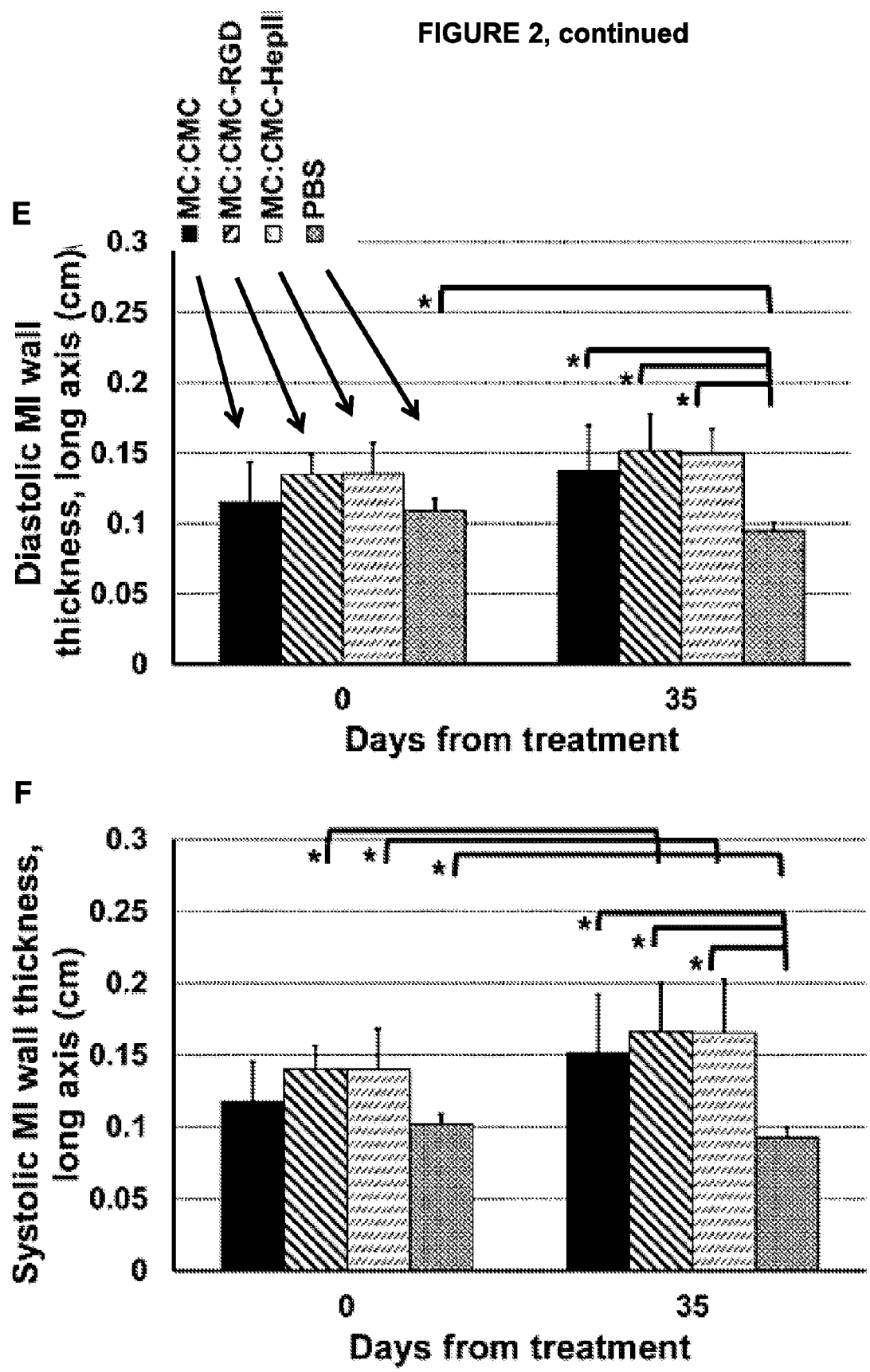
FIGURE 2, continued

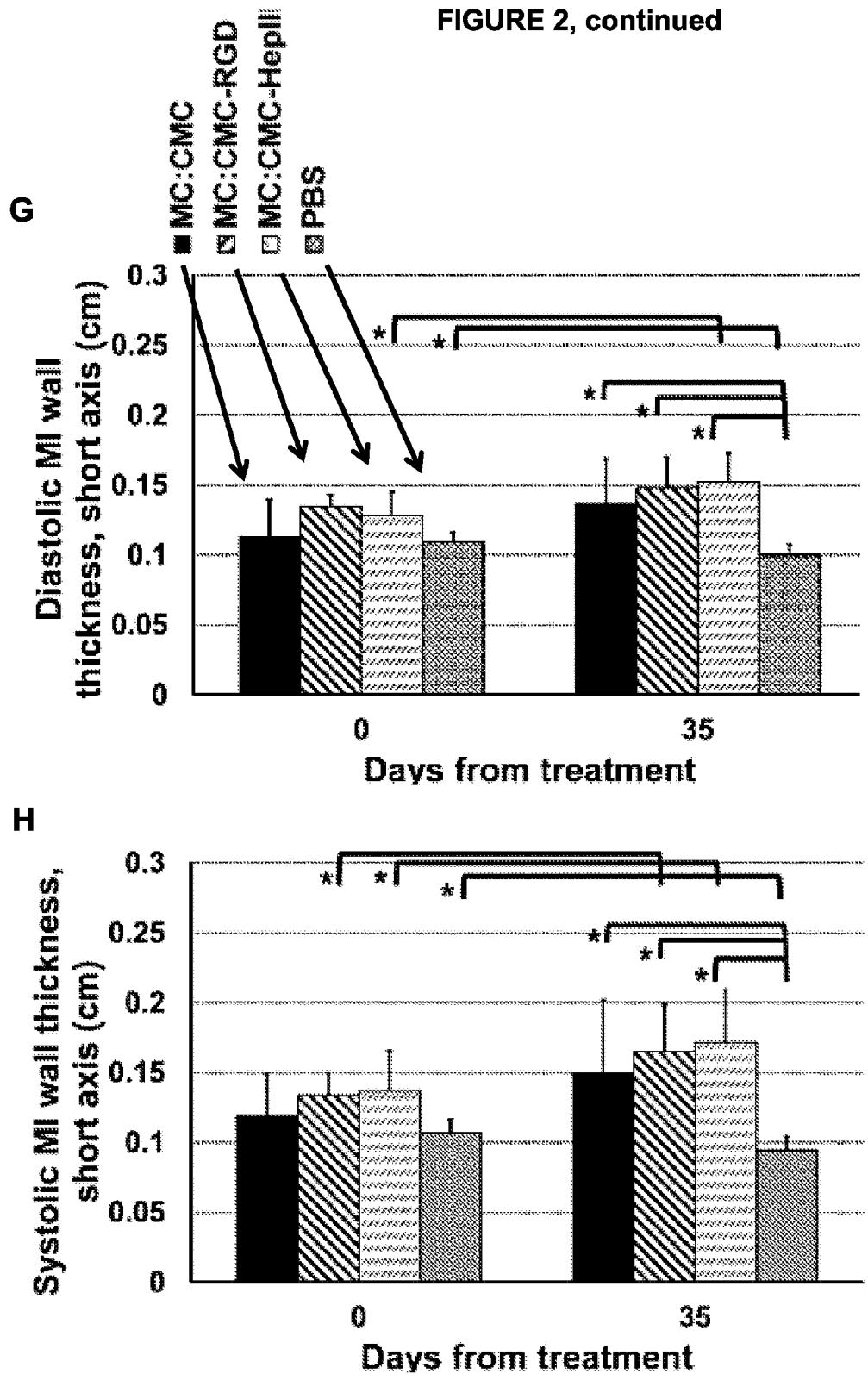
FIGURE 2, continued

Figure 3:
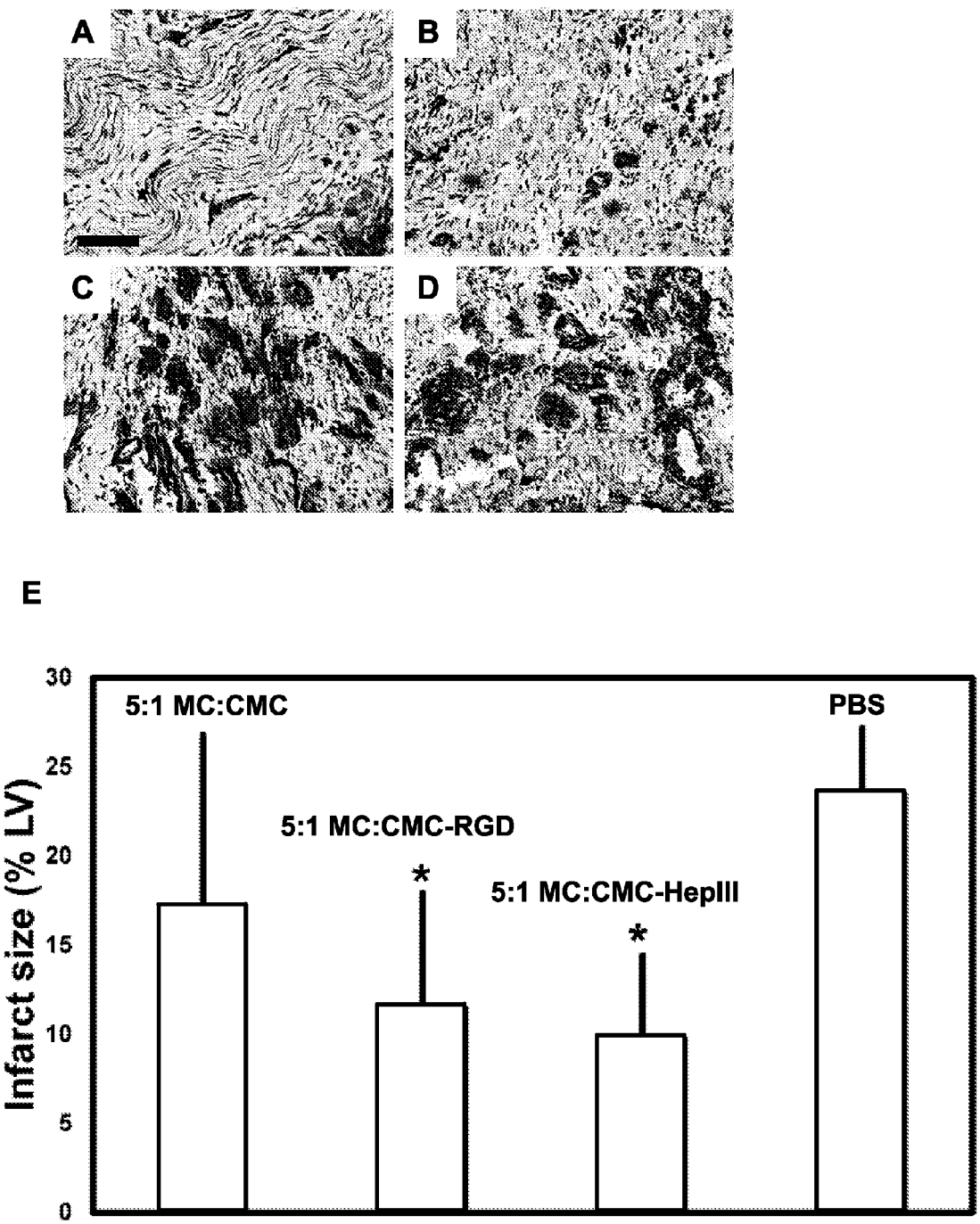

FIGURE 3, continued
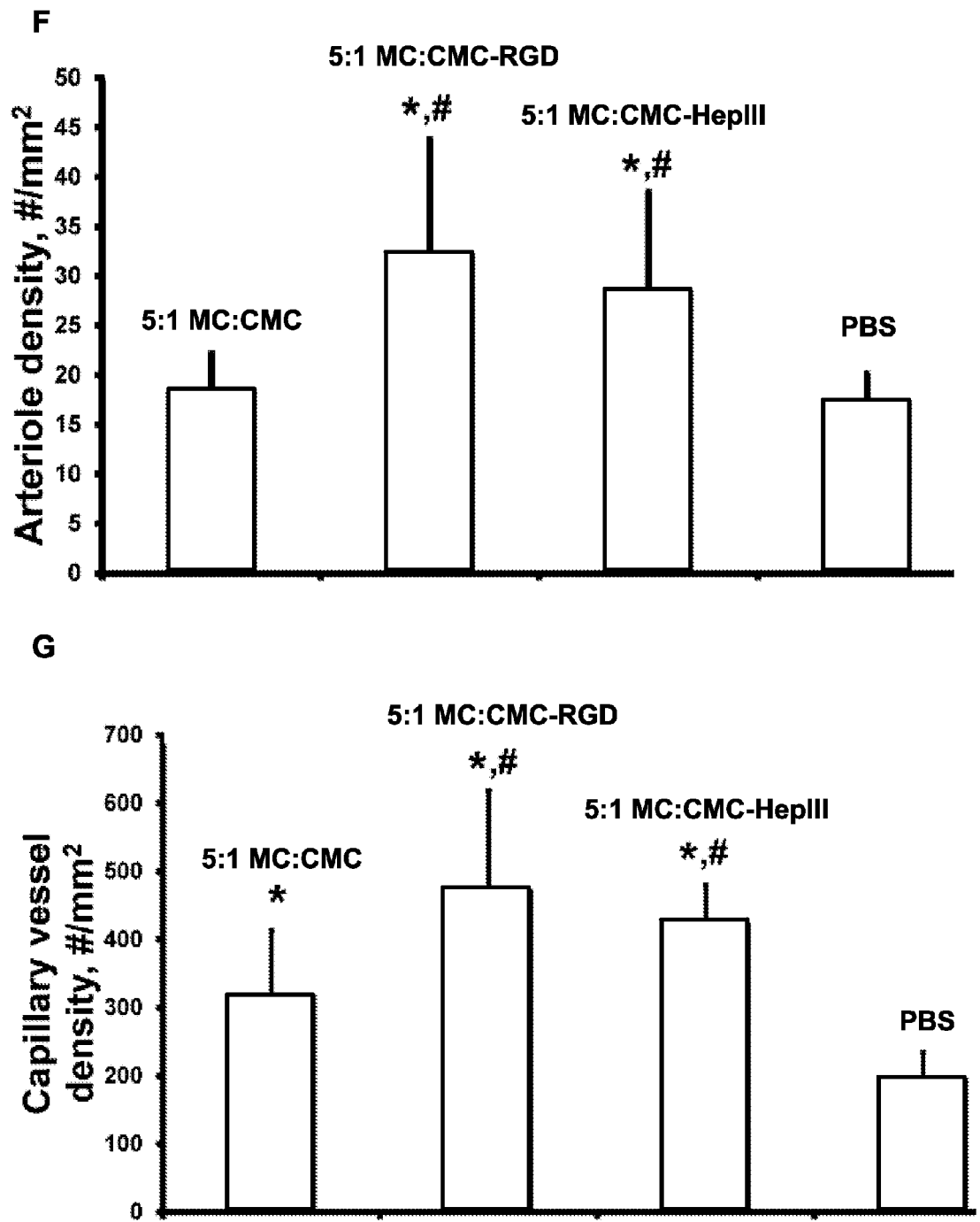

Figure 4:
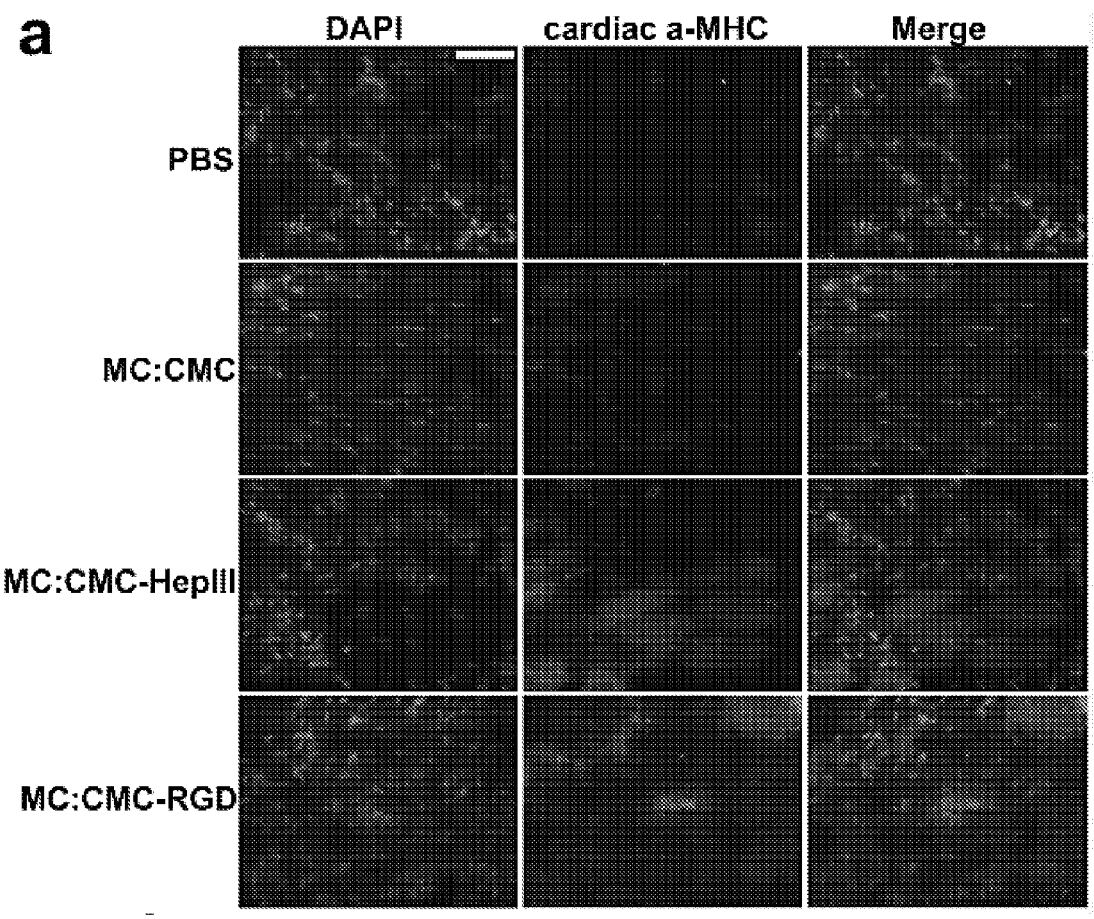

FIGURE 4, continued
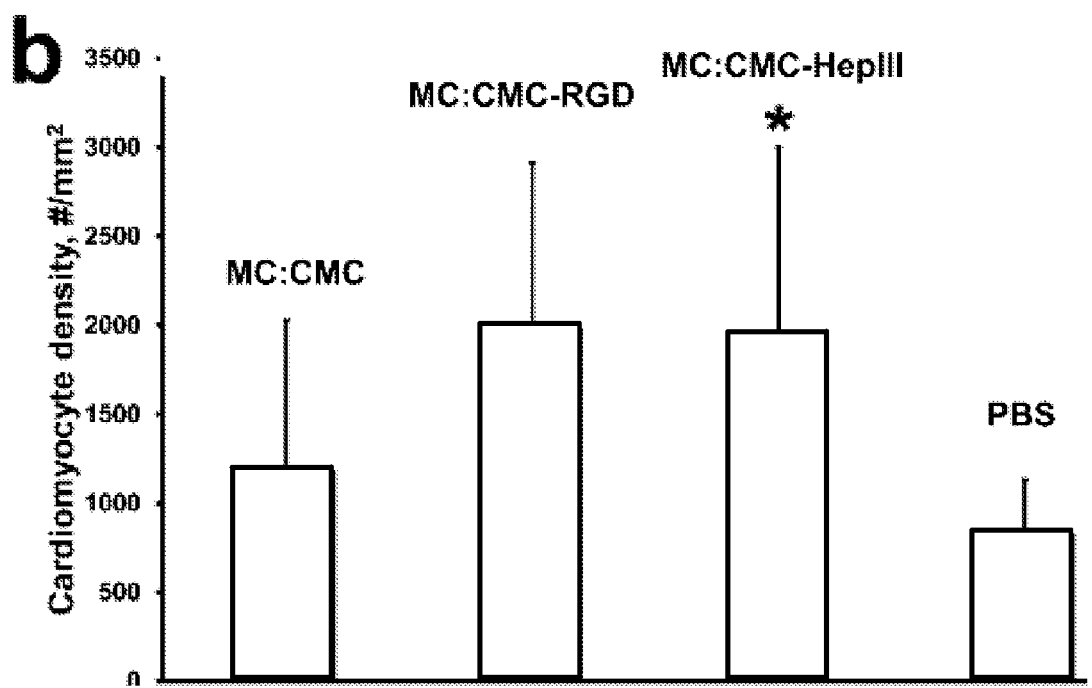

CARBOXYMETHYLCELLULOSE-PEPTIDE CONJUGATES AND METHODS FOR USING THE SAME

CROSS-REFERENCE TO RELATED APPLICATION

Pursuant to 35 U.S.C. § 119(e), this application claims priority to the filing date of U.S. Provisional Patent Application Ser. No. 61/843,789, filed Jul. 8, 2013, the disclosure of which is herein incorporated by reference.

INTRODUCTION

Organ or tissue injury remains a frequent, costly, and serious problem in health care despite advances in medical technology. Available treatments include organ transplantation, surgical reconstruction, mechanical devices (e.g., pace makers and kidney dialysis machines), drug therapy, and tissue engineering. These treatments, however, are not perfect solutions. Organ transplantation is limited by the availability of donors and complications such as tissue rejection. Surgical reconstruction is costly, highly invasive, and not always effective. Mechanical devices cannot functionally replace an organ, for example, dialysis machines can only help to remove some of the metabolic waste from the body. Likewise, maintaining drug concentration levels in vivo, comparable to the control systems of the body, are difficult to achieve. Finally, tissue engineering while promising, is encumbered by size limitations that typically require the assembly of the engineered tissue in vitro, followed by surgical implantation in vivo.

An example of a common organ or tissue injury is cardiovascular disease (CVD), which is the leading cause of death worldwide. Despite advances in the medical management of patients with coronary heart disease, the incidence of heart failure continues to increase with roughly 6 million people in the United States diagnosed with heart failure and nearly 550,000 new cases of heart failure occurring annually. With a 5-year mortality rate of 50% in patients with advanced heart failure, new therapies are being sought to reverse the natural progression of the disease.

Based on Laplace's law, left ventricular (LV) dilatation and wall thinning leads to increased wall stress, which is a major factor in the progression of heart failure. Heart failure following a myocardial infarction (MI) is often progressive. Scar tissue formation and aneurismal thinning of the infarct region often occur in patients who survive myocardial infarctions. The death of cardiomyocytes may result in negative left ventricular (LV) remodeling which leads to increased wall stress in the remaining viable myocardium. This process results in a sequence of molecular, cellular, and physiological responses which lead to LV dilation. Although the exact mechanisms of heart failure are unknown, LV remodeling is generally considered an independent contributor to its progression.

SUMMARY

Provided are compositions for repairing an injured tissue. The composition includes carboxymethylcellulose conjugated to an extracellular matrix derived peptide, and a methylcellulose. Also provided are kits and methods for using the subject compositions.

BRIEF DESCRIPTION OF THE FIGURES

FIG. 1 (Panels A-B) presents a rheological analysis of the unmodified and peptide-modified 5:1 MC:CMC polymer blends.

FIG. 2 (Panels A-H) presents echocardiography data.

FIG. 3 (Panels A-G) presents an immunohistological assessment of injured hearts. Representative images of staining for capillaries and arterioles within the infarct region of hearts from rats treated with (a) PBS, (b) unmodified MC:CMC, (c) MC:CMC-HepIII, or (d) MC:CMC-RGD.

FIG. 4 (Panels A-B) presents an assessment of cardiomyocytes within the MI region.

Before the present invention is described in greater detail, it is to be understood that this invention is not limited to the particular embodiments described, and as such may, of course, vary. It is also to be understood that the terminology used herein is for the purpose of describing particular embodiments only, and is not intended to be limiting, since the scope of the present invention is embodied by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, it will be readily apparent to one of ordinary skill in the art in light of the teachings herein that certain changes and modifications may be made thereto without departing from the spirit and scope of the appended claims. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. To the extent such publications may set out definitions of a term that conflicts with the explicit or implicit definition of the present disclosure, the definition of the present disclosure controls. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

DETAILED DESCRIPTION

Provided are compositions for repairing an injured tissue. The composition includes carboxymethylcellulose (CMC) conjugated to an extracellular matrix derived (EMD) peptide, and a methylcellulose (MC). Also provided are kits and methods for using the subject compositions.

Below, the compositions are described first in greater detail, followed by a review of the methods in which the compositions find use, as well as a discussion of various representative applications in which the compositions and methods find use.

Compositions

Embodiments of the present disclosure include a composition for repairing an injured tissue. The composition includes a carboxymethylcellulose (CMC) conjugated to a peptide (e.g., an extracellular matrix (ECM) peptide).

Carboxymethylcellulose is a cellulose derivative with carboxymethyl groups (—CH$_2$COOH) bound to one or more of the hydroxyl groups of the glucopyranose monomers that make up the cellulose backbone. The chemical structure of CMC is shown below.

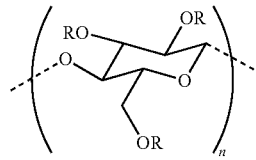

where R is H or —CH$_2$COOH.

In certain embodiments, CMC is a polymer of glucopyranose monomers and has an average molecular weight ranging from 5 kDa to 1000 kDa. By "average" is meant the arithmetic mean. For example, CMC may have an average molecular weight ranging from 10 kDa to 1000 kDa, such as 25 kDa to 1000 kDa, including 50 kDa to 1000 kDa, or 50 kDa to 950 kDa, or 50 kDa to 900 kDa, or 50 kDa to 850 kDa, or 50 kDa to 800 kDa, or 50 kDa to 750 kDa, or 50 kDa to 700 kDa, or 50 kDa to 650 kDa, or 50 kDa to 600 kDa, or 50 kDa to 550 kDa, or 50 kDa to 500 kDa, or 50 kDa to 450 kDa, or 50 kDa to 400 kDa, or 50 kDa to 350 kDa, or 50 kDa to 300 kDa, or 50 kDa to 250 kDa, or 50 kDa to 200 kDa, or 50 kDa to 150 kDa, or 50 kDa to 100 kDa. In certain embodiments, CMC has an average molecular weight ranging from 50 kDa to 100 kDa, such as 90 kDa. In some instances, in the structural formula above, n has a value appropriate to provide a CMC having an average molecular weight in the ranges described above. For instance, n may range from 10 to 10,000, such as 25 to 10,000, including 50 to 10,000, or 75 to 10,000, or 100 to 10,000, or 150 to 10,000, or 200 to 10,000, or 250 to 10,000, or 250 to 9000, or 250 to 8500, or 250 to 8000, or 250 to 7500, or 250 to 7000, or 250 to 6500, or 250 to 6000, or 250 to 5500, or 250 to 5000, or 250 to 4500, or 250 to 4000, or 250 to 3500, or 250 to 3000, or 250 to 2500, or 250 to 2000, or 250 to 1500, or 250 to 1000, or 250 to 500. In some cases, n may range from 250 to 500, such as 475.

As shown in the chemical structure of CMC above, each glucopyranose monomer in CMC may have 0, 1, 2 or 3 carboxymethyl groups per glucopyranose monomer. The number of carboxymethyl groups per glycopyranose monomer is referred to as the degree of substitution (DS). For instance, a CMC polymer may have a degree of substitution ranging from 0.1 to 3, such as 0.1 to 2.5, including 0.1 to 2, or 0.1 to 1.5, or 0.1 to 1, or 0.2 to 1, or 0.3 to 1, or 0.4 to 1, or 0.5 to 1, or 0.5 to 0.9, or 0.6 to 0.9, or 0.7 to 0.9. In certain embodiments, the CMC polymer has a DS ranging from 0.6 to 0.9.

In certain embodiments, CMC is conjugated to a peptide to form a CMC-peptide conjugate. By conjugated is meant that the CMC is bonded to the peptide. Bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. In certain embodiments, the CMC is covalently bonded to the peptide. For example, the covalent bond between the CMC and the peptide may be an amide bond, such as an amide bond between a carboxymethyl group of CMC and an amino group of the peptide. The amide bond between CMC and the peptide may be formed at an internal amino acid residue of the peptide, where the internal amino acid residue includes an amino group. In other instances, the amide bond between CMC and the peptide is formed at the N-terminal amino group of the peptide. In certain embodiments, the CMC-peptide conjugate includes an amide bond between a carboxymethyl group of CMC and an N-terminal amino group of the peptide, as shown in the structure below.

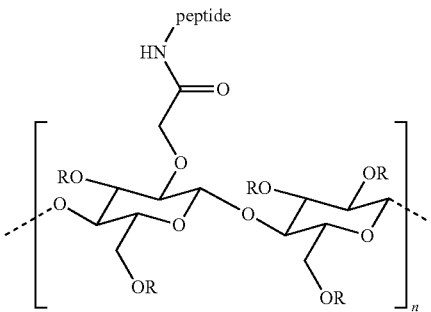

where R is H or —CH$_2$COOH.

In certain embodiments, the CMC is indirectly bound to the peptide. By "indirect binding" or "indirectly bound" is meant that the CMC is bound to the peptide through one or more linker moieties. For instance, the CMC may be bound to the peptide through a linker moiety, such as, but not limited to, polyethylene glycol (PEG), methacrylate, and the like, and combinations thereof. In other embodiments, the CMC is directly bound to the peptide. By "direct binding" or directly bound" is meant that the CMC is bound to the peptide without any intervening linker moieties. For example, the CMC-peptide conjugate may include CMC directly bonded to the peptide without an intervening linker moiety, such as PEG, methacrylate, or the like. In certain instances, as discussed above, the CMC may be covalently bonded directly to the peptide, such as through an amide bond between a carboxymethyl group of CMC and an amino group of the peptide. In certain embodiments, the CMC-peptide conjugate includes an amide bond directly between a carboxymethyl group of CMC and an amino group (e.g., an N-terminal amino group) of the peptide, as shown in the structure above.

In some embodiments, the composition includes one or more additional polymers. For example, the composition may include a second cellulose-based polymer, such as, but not limited to methylcellulose (MC), ethylcellulose, hydroxypropylcellulose (HPC), hydroxypropylmethylcellulose (HPMC), and the like, and combinations thereof. In certain embodiments, one or more additional polymers may be included in the composition, such as polymers including, but not limited to, polyethylene oxide ("PEO"), PEO-poly-1-lactic acid ("PLLA-PEO block copolymer"), poly(N-isopropylacrylamide-co-acrylic acid) ("poly(NIPAAm-co-Aac)"), pluronics, poly-(N-vinyl-2-pyrrolidone) ("PVP"), and the like, and combinations thereof.

In certain embodiments, the composition includes methylcellulose. The chemical structure of methylcellulose is shown below.

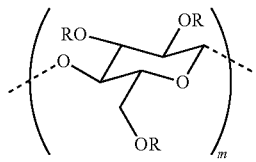

where R is H or —$CH_3$.

Thus, in some cases, the composition may include CMC and MC. The CMC and MC may be present in the composition as a mixture (e.g., a homogeneous mixture) of CMC and MC. In other embodiments, the CMC and MC may be crosslinked.

In certain embodiments, methylcellulose is a polymer of glucopyranose monomers and has an average molecular weight ranging from 1 kDa to 100 kDa. For example, MC may have an average molecular weight ranging from 1 kDa to 100 kDa, such as 5 kDa to 100 kDa, including 5 kDa to 95 kDa, or 5 kDa to 90 kDa, or 10 kDa to 90 kDa, or 10 kDa to 85 kDa, or 10 kDa to 80 kDa, or 10 kDa to 75 kDa, or 10 kDa to 70 kDa, or 10 kDa to 65 kDa, or 10 kDa to 60 kDa, or 10 kDa to 55 kDa, or 10 kDa to 50 kDa, or 10 kDa to 45 kDa, or 10 kDa to 40 kDa, or 10 kDa to 35 kDa, or 10 kDa to 30 kDa, or 10 kDa to 25 kDa, or 10 kDa to 20 kDa. In certain embodiments, the MC has an average molecular weight ranging from 10 kDa to 20 kDa, such as 15 kDa. In some instances, in the structural formula above, m has a value appropriate to provide a MC having an average molecular weight in the ranges described above. For instance, m may range from 5 to 1000, such as 10 to 1000, including 20 to 1000, or 25 to 1000, or 25 to 950, or 25 to 900, or 25 to 850, or 25 to 800, or 25 to 750, or 25 to 700, or 25 to 650, or 25 to 600, or 25 to 550, or 25 to 500, or 30 to 500, or 40 to 500, or 50 to 500, or 50 to 450, or 50 to 400, or 50 to 350, or 50 to 300, or 50 to 250, or 50 to 200, or 50 to 150. In certain embodiments, m ranges from 50 to 150, such as 90.

As shown in the chemical structure of methylcellulose above, each glucopyranose monomer in MC may have 0, 1, 2 or 3 methoxy groups per glucopyranose monomer. The number of methoxy groups per glycopyranose monomer (i.e., degree of substitution, DS) for MC may range from 0.1 to 3, such as 0.1 to 2.7, including 0.1 to 2.5, or 0.3 to 2.5, or 0.5 to 2.5, or 0.5 to 2.2, or 0.5 to 2, or 0.7 to 2, or 1 to 2, or 1.2 to 2, or 1.5 to 2. In certain embodiments, the MC polymer has a DS ranging from 1.5 to 2.

In certain embodiments, the composition includes CMC and MC with a certain ratio (w/w) of MC:CMC. In some cases, the MC:CMC ratio (w/w) is 1:10, or 1:9, or 1:8, or 1:7, or 1:6, or 1:5, or 1:4, or 1:3, or 1:2, or 1:1, or 2:1, or 3:1, or 4:1, or 5:1, or 6:1, or 7:1, or 8:1, or 9:1, or 10:1. For example, the MC:CMC ratio (w/w) may range from 1:1 to 10:1, such as 2:1 to 10:1, including 3:1 to 10:1, or 4:1 to 10:1, or 4:1 to 9:1, or 4:1 to 8:1, or 4:1 to 7:1, or 4:1 to 6:1. In certain embodiments, the MC:CMC ratio (w/w) is 5:1.

As described above, in certain embodiments, the composition includes a CMC-peptide conjugate. Thus, in some instances, the composition includes the CMC-peptide conjugate and one or more additional polymers as described above. In certain cases, the composition includes the CMC-peptide conjugate and methylcellulose.

In certain embodiments, the composition includes the CMC-peptide conjugate and MC with a certain ratio (w/w) of MC:CMC-peptide conjugate. In some cases, the MC:CMC-peptide conjugate ratio (w/w) is 1:10, or 1:9, or 1:8, or 1:7, or 1:6, or 1:5, or 1:4, or 1:3, or 1:2, or 1:1, or 2:1, or 3:1, or 4:1, or 5:1, or 6:1, or 7:1, or 8:1, or 9:1, or 10:1. For example, the MC:CMC-peptide conjugate ratio (w/w) may range from 1:1 to 10:1, such as 2:1 to 10:1, including 3:1 to 10:1, or 4:1 to 10:1, or 4:1 to 9:1, or 4:1 to 8:1, or 4:1 to 7:1, or 4:1 to 6:1. In certain embodiments, the MC:CMC-peptide conjugate ratio (w/w) is 5:1.

In certain embodiments, the CMC is conjugated to a peptide as described above. In some cases, the CMC is conjugated to one peptide. In other embodiments, the CMC may be conjugated to two or more peptides. For instance, the CMC may be conjugated to two or more peptides at two or more conjugation sites on CMC. For example, as described above, the CMC may be conjugated to the peptides through an amide bond to each peptide formed between a carboxymethyl group of CMC and an amino group of each peptide (e.g., an N-terminal amino group). In some cases, the CMC in the composition is conjugated to one or more peptides, where the peptides are the same peptide (e.g., multiple copies of the peptides having the same amino acid sequence). In other embodiments, the CMC in the composition is conjugated to one or more peptides, where the peptides are different peptides. In other embodiments, the composition includes a mixture of different CMC-peptide conjugates. For example, the composition may include a first CMC-peptide conjugate, where the first CMC is conjugated to a first peptide, and a second CMC-peptide conjugate, where the second CMC is conjugated to a different peptide. Peptides suitable for compositions of the present disclosure are described in more detail below.

In certain embodiments, the composition includes from 0.1 mg to 100 mg peptide per gram MC:CMC, such as 0.1 mg to 90 mg peptide, including 0.1 mg to 80 mg peptide, or 0.1 mg to 70 mg peptide, or 0.1 mg to 60 mg peptide, or 0.1 mg to 50 mg peptide, or 0.1 mg to 40 mg peptide, or 0.1 mg to 30 mg peptide, or 0.1 mg to 25 mg peptide, or 0.1 mg to 20 mg peptide, or 0.1 mg to 15 mg peptide, or 0.1 mg to 10 mg peptide, or 0.1 mg to 5 mg peptide, or 0.1 mg to 4 mg peptide, or 0.1 mg to 3 mg peptide, or 0.1 mg to 2 mg peptide, or 0.1 mg to 1 mg peptide, or 0.1 mg to 1 mg peptide, or 0.2 mg to 1 mg peptide, or 0.3 mg to 1 mg peptide, or 0.4 mg to 1 mg peptide, or 0.5 mg to 1 mg peptide per gram of MC:CMC. In certain instances, the composition includes 0.5 mg to 1 mg peptide per gram of MC:CMC, such as 0.6 mg peptide per gram of MC:CMC.

In certain embodiments, the composition has viscoelastic properties sufficient to provide structural and/or geometric support to a body tissue, such as a cardiac tissue (e.g., a cardiac tissue of an infarct region). For example, the composition may have an elastic modulus sufficient to provide structural and/or geometric support to a body tissue. The elastic modulus (i.e., storage modulus) is a mathematical description of a substance's tendency to be deformed elastically (i.e., non-permanently) when a force is applied to it. A stiffer material will have a higher elastic modulus. In some cases, the composition has an elastic modulus ranging from 0.01 kPa to 50 kPa. In certain instances, the elastic modulus of the composition is dependent on the temperature. For instance, the elastic modulus of the composition may increase with increasing temperature. In some cases, the elastic modulus of the composition increases from 0.01 kPa at a temperature of 20° C. to 20 kPa at a temperature of 40° C. A graph of the elastic modulus of compositions according to the present disclosure is shown in FIG. 1(a).

In some cases, the composition has an elastic modulus ranging from 0.01 kPa to 50 kPa, such as 0.02 kPa to 50 kPa, including 0.03 kPa to 50 kPa, or 0.04 kPa to 50 kPa, or 0.05 kPa to 50 kPa, or 0.06 kPa to 50 kPa, or 0.07 kPa to 50 kPa, or 0.08 kPa to 50 kPa, or 0.09 kPa to 50 kPa, or 0.1 kPa to 50 kPa, or 0.1 kPa to 40 kPa, or 0.1 kPa to 30 kPa, or 0.1 kPa to 20 kPa, or 0.1 kPa to 15 kPa, or 0.1 kPa to 10 kPa, or 0.2 kPa to 10 kPa, or 0.3 kPa to 10 kPa, or 0.4 kPa to 10 kPa, or 0.5 kPa to 10 kPa, or 0.6 kPa to 10 kPa, or 0.7 kPa to 10 kPa, or 0.8 kPa to 10 kPa, or 0.9 kPa to 10 kPa, or 1 kPa to 10 kPa, or 1.5 kPa to 10 kPa, or 2 kPa to 10 kPa, or 2.5 kPa to 10 kPa, or 3 kPa to 10 kPa, or 3.5 kPa to 10 kPa, or 4 kPa to 10 kPa, or 4.5 kPa to 10 kPa, or 5 kPa to 10 kPa at a temperature of 37° C. In certain embodiments, the composition has an elastic modulus ranging from 1 kPa to 10 kPa at a temperature of 37° C.

In some cases, the composition has a viscous modulus sufficient to provide structural and/or geometric support to a body tissue, such as a cardiac tissue (e.g., a cardiac tissue of an infarct region). The viscous modulus (i.e., loss modulus) of a material describes the viscous properties of the material. For example, the viscosity of a material is a measure of its resistance to gradual deformation by shear stress or tensile stress. In some cases, the composition has a viscous modulus ranging from 0.01 kPa to 10 kPa. In certain instances, the viscous modulus of the composition is dependent on the temperature. For instance, the viscous modulus of the composition may increase with increasing temperature. In some cases, the viscous modulus of the composition increases from 0.03 kPa at a temperature of 20° C. to 5 kPa at a temperature of 40° C. A graph of the viscous modulus of compositions according to the present disclosure is shown in FIG. 1(b).

In some cases, the composition has a viscous modulus ranging from 0.01 kPa to 10 kPa, such as 0.02 kPa to 10 kPa, including 0.03 kPa to 10 kPa, or 0.04 kPa to 10 kPa, or 0.05 kPa to 10 kPa, or 0.06 kPa to 10 kPa, or 0.07 kPa to 10 kPa, or 0.08 kPa to 10 kPa, or 0.09 kPa to 10 kPa, or 0.1 kPa to 10 kPa, or 0.2 kPa to 10 kPa, or 0.3 kPa to 10 kPa, or 0.4 kPa to 10 kPa, or 0.5 kPa to 10 kPa, or 0.5 kPa to 9 kPa, or 0.5 kPa to 8 kPa, or 0.5 kPa to 7 kPa, or 0.5 kPa to 6 kPa, or 0.5 kPa to 5 kPa, or 0.5 kPa to 4 kPa, or 0.5 kPa to 3 kPa, or 0.5 kPa to 2 kPa, or 0.5 kPa to 1 kPa at a temperature of 37° C. In certain embodiments, the composition has a viscous modulus ranging from 0.1 kPa to 1 kPa at a temperature of 37° C.

In certain embodiments, the composition has a gelling (e.g., polymerization) temperature similar to the normal body temperature of a subject, such as similar to human body temperature, or 37° C. By gelling temperature is meant the point on intersection between the plot for the elastic modulus and the plot for the viscous modulus. In some cases, if the composition is below the gelling temperature, then the composition has a relatively low viscosity, such as in the form of a liquid. In some instances, if the composition is above the gelling temperature, then the composition increases in viscosity (e.g., polymerizes), such that the composition is in the form of a gel. Compositions that transition from a liquid to a gel may facilitate administration of the composition to the subject, for example by facilitating injection of a low viscosity (e.g., liquid) composition at a temperature below the gelling temperature. After injection of the composition to the target treatment site, the temperature of the composition may increase due to absorption of heat from the surrounding body tissue, such that the composition increases in viscosity (e.g., transitions from a liquid to a gel, or polymerizes), thus providing structural and/or geometric support to the body tissue at the target treatment site. In some instances, gelling of the composition at the target treatment site may also facilitate retention of the composition at the treatment site by reducing the diffusion and/or migration of the composition away from the treatment site. In certain embodiments, the composition has a gelling temperature of 30° C. to 40° C., such as from 32° C. to 40° C., including from 35° C. to 40° C. In certain instances, the composition has a gelling temperature of 37° C.

In certain embodiments, the viscosity of the composition increases with increasing temperature, as described above. In some cases, the viscosity of the composition decreases with decreasing temperature. For example, if the composition is above the gelling temperature, then the composition has a relatively high viscosity, such as in the form of a gel. In some instances, if the composition is cooled to below the gelling temperature, then the composition decreases in viscosity, such as in the form of a liquid. As such, compositions of the present disclosure are reversible polymers (e.g., thermoreversible polymers), where the transition from liquid to gel may be reversed upon exposure to appropriate conditions. For instance, as described above, compositions of the present disclosure include thermoreversible polymers, where the viscosity of the composition may be changed depending on the temperature of the composition.

In certain embodiments, the composition does not include a photocrosslinkable polymer. For instance, the composition may not include a polymer where polymerization is initiated by exposure to light, such as visible or UV light. As described above, rather than polymerizing in response to exposure to light, compositions of the present disclosure may change viscosity (e.g., polymerize) in response to changes in temperature.

Peptides

Peptides suitable for conjugation to CMC for use in the compositions and methods of the present disclosure exhibit one or more of the following properties: (i) a positive effect on cell attachment; (ii) a positive effect on cell activation; (iii) a positive chemotropic property; and (iv) a positive effect on angiogenesis. Assays (e.g., cell attachment assays, cell activation assays, chemotropic assays, and angiogenic assays) to determine whether a peptide is suitable for the subject compositions and methods include those described in the U.S. patent application US20100291080, which is hereby incorporated by reference in its entirety.

In some embodiments, a suitable peptide is an ECM peptide. The term "ECM peptide" is used herein to refer to a peptide fragment derived from an extracellular matrix (ECM) protein or a variant thereof. ECM proteins of interest include naturally-occurring ECM proteins, such as those secreted by cells, which proteins provide various physical and functional attributes (e.g., elasticity, rigidity, connectivity, resistance to tensile forces, etc.) to the surrounding extracellular matrix by incorporating into the ECM and/or interacting with ECM components. Examples of extracellular matrix proteins for deriving a suitable ECM peptide include, but are not limited to: fibrinogen, fibronectin, fibrin, collagen (Types I, II, III, and IV), laminin, elastin, and Tenascin-C.

While full length proteins from which an ECM peptide can be derived may exhibit one or more of the above properties, not all ECM peptides derived from these proteins exhibit these properties. Examples of ECM peptides suitable for use with the compositions and methods of the present disclosure include, but are not limited to: "RGD peptide" (GRGDSPASSPISC; SEQ ID NO:1); HepI (TAGSCLRKFSTMY; SEQ ID NO: 4); and HepIII (GEFYFDLRLKGDKY; SEQ ID NO: 2).

A suitable ECM peptide has a length, in amino acid residues, that ranges from about 5 to about 100 (e.g., from about 5 to about 75, from about 5 to about 50, from about 5 to about 30, from about 5 to about 20, from about 5 to about 15, from about 10 to about 100, from about 10 to about 75, from about 10 to about 50, from about 10 to about 30, from about 10 to about 20, from about 12 to about 20, from about 12 to about 17, from about 12 to about 15, from about 13 to about 20, from about 13 to about 17, from about 13 to about 15, about 5, about 6, or about 7, about 8, about 9 about 10, about 11, or about 12, about 13, about 14, or about 15).

A suitable ECM peptide can comprise an RGD motif (Arginine-Glycine-Aspartic acid). The RGD motif is known to mediate cell attachment and is found in numerous proteins. For example, some integrins recognize the RGD motif within their ligands, and the binding of integrins to the RGD motif mediates both cell-substratum and cell-cell interactions. A suitable ECM peptide can comprise, as non-limiting examples, the amino acid sequences RGD, GRGDS (SEQ ID NO: 14), RGDV (SEQ ID NO: 15), RGDS (SEQ ID NO: 19), RGDF (SEQ ID NO: 20), GRGDY (SEQ ID NO: 25), GRGDSP (SEQ ID NO: 26), GGGGRGDSP (SEQ ID NO: 28) and/or GGGGRGDY (SEQ ID NO: 29). A suitable ECM peptide can have flanking amino acids to the C-terminal or N-terminal side of the above amino acid sequences. One non-limiting example of a suitable RGD-motif containing ECM peptide is the RGD peptide GRGDSPASSPISC (SEQ ID NO: 1).

The amino acid sequence of a suitable ECM peptide can comprise a heparin binding domain. Non-limiting examples of suitable ECM peptides having a heparin biding domain are the HepI peptide TAGSCLRKFSTMY (SEQ ID NO: 4) and the HepIII peptide GEFYFDLRLKGDKY (SEQ ID NO: 2).

Suitable ECM peptides can comprise RGD, YIGSR (SEQ ID NO: 9), IKVAV (SEQ ID NO: 10), REDV (SEQ ID NO: 11), DGEA (SEQ ID NO: 12), VGVAPG (SEQ ID NO: 13), GRGDS (SEQ ID NO: 14), LDV, RGDV (SEQ ID NO: 15), PDSGR (SEQ ID NO: 16), RYVVLPR (SEQ ID NO: 17), LGTIPG (SEQ ID NO: 18), LAG, RGDS (SEQ ID NO: 19), RGDF (SEQ ID NO: 20), HHLGGALQAGDV (SEQ ID NO: 21), VTCG (SEQ ID NO: 22), SDGD (SEQ ID NO: 23), GREDVY (SEQ ID NO: 24), GRGDY (SEQ ID NO: 25), GRGDSP (SEQ ID NO: 26), VAPG (SEQ ID NO: 27), GGGGRGDSP (SEQ ID NO: 28), GGGGRGDY (SEQ ID NO: 29) and/or FTLCFD (SEQ ID NO: 30).

In some embodiments, a suitable ECM peptide is derived from a fibronectin protein. Fibronectin, is a large glycoprotein dimer composed of two large subunits joined at one end by a disulfide bond. Each subunit folds into a series of functionally distinct domains, separated by regions of flexible polypeptide chain. Among the functional domains contained within fibronectin molecule are a self-association domain, collagen binding domain, heparin binding domain and a cell binding domain. A central feature of the cell binding domain is the RGD (arginine-glycine-aspartic acid) binding motif, which provides sites for cell attachment via the α5β1 and α8β1 integrin receptors. One non-limiting example of a suitable ECM peptide derived from Fibronectin is the RGD peptide GRGDSPASSPISC (SEQ ID NO: 1). In some embodiments, a suitable ECM peptide, derived from Fibronectin, is the FC/HV peptide (WQPPRARI, SEQ ID NO: 3), which is found in the C-terminal heparin binding and cell adhesion promoting domain of a fragment of fibronectin.

In some embodiments, a suitable ECM peptide is derived from a collagen protein. Collagens provide structural integrity by resisting mechanical loading forces and degradation. Type I collagen is prevalent in a variety of tissue types including bone, skin and various internal organs and promotes cell growth and differentiation via binding of α1β1 and α2β1. Type II collagen is present in cartilage and binds to chondrocytes through the α2β1 integrin. Type IV collagen is a component of the basal lamina and binds cells through the α1β1 and α2β1 integrins. Non-limiting examples of a suitable ECM peptides derived from collagen IV are the HepI peptide TAGSCLRKFSTMY (SEQ ID NO: 4), and the HepIII peptide GEFYFDLRLKGDKY (SEQ ID NO: 2). HepI is found a fragment from the NC1 domain of Collagen IV while HepIII is a fragment of the helical domain of Collagen IV.

In some embodiments, a suitable ECM peptide is derived from an elastin protein. Elastin is a principal component of the basal lamina and the ECM. Elastin polypeptide chains are cross-linked together to form rubber like, elastic fibers. Each elastin molecule uncoils into a more extended conformation when the fiber is stretched and will recoil spontaneously as soon as the stretching force is relaxed. Elastin combines with collagen to give tissue its shape, rigidity, and flexibility. One non-limiting example of a suitable ECM peptide derived from Elastin is VGVAPG (SEQ ID NO: 5).

In some embodiments, a suitable ECM peptide is derived from fibrinogen. Fibrinogen is a soluble glycoprotein that is converted by thrombin into fibrin during blood clot formation. Fibrin contains the arg-gly-asp (RGD) motif that binds to the α5β1 and α8β1 integrin receptors.

In some embodiments, a suitable ECM peptide is derived from a laminin protein. Laminin is a large flexible protein composed of three long polypeptide chains arranged in the shape of an asymmetric cross and held together by disulfide bonds. Several isoforms of each type of chain can associate in different combinations to form a large family of laminin proteins that are useful in deriving a suitable ECM peptide. Laminin, like type IV collagen, can self-assemble into felt-like sheets and binds cells through α6β1 and α7β1 integrin receptors. Non-limiting examples of suitable ECM peptides derived from Laminin are LGTIPG (SEQ ID NO: 6); YIGSR (SEQ ID NO: 7); IKVAV (SEQ ID NO: 10); AG73 (RKRLQVQLSIRT; SEQ ID NO: 31); C16 (KAFDITYVRLKF; SEQ ID NO: 32); and LSNIDYILIKAS (SEQ ID NO: 8).

In some embodiments, a suitable ECM peptide is derived from a Tenascin-C protein. Tenascin-C is comprised of multiple repeats of short amino acid sequences that form functional domains. Tenascin-C may be adhesive or non-adhesive, depending on the cell type. Tenascin-C is known to interact with the α8β1 and α9β1 integrins and to stimulate the synthesis and secretion of proteases. One non-limiting example of a suitable ECM peptide derived from Tenascin-C is WYRNCHRVNLMGRYGDNNHSQGVNWFHWKG (SEQ ID NO: 33).

Any convenient method may be used to derive a suitable peptide (e.g., a suitable ECM peptide) from a longer (e.g., full length) polypeptide (e.g., an ECM protein), and such methods will be known to one of ordinary skill in the art. In some embodiments, a protein (e.g., an ECM protein) may be enzymatically cleaved using a protease, such as trypsin, to generate a suitable peptide (e.g., a suitable ECM peptide). In some embodiments, peptides (e.g., ECM peptides) may be identified using bioinformatic analysis and the identified peptide then produced through recombinant means. In some embodiments, a suitable peptide (e.g., a suitable ECM peptide) is a "variant peptide" (e.g., a "variant ECM peptide"). A variant peptide comprises a mutation (e.g., a substitution, insertion, deletion, inversion, etc.) relative to a naturally occurring wild-type protein sequence. In some such cases, the mutation improves the functional characteristics of the peptide. Polypeptides suitable for deriving a suitable peptide can be purified from donor sources; purchased from commercial suppliers; or produced by recombinants means.

General Synthetic Scheme

Conjugates according to embodiments of the present disclosure may be formed using any convenient synthetic method for forming covalent bonds between a cellulose polymer and a peptide, such as a carboxymethylcellulose polymer and a peptide. In certain embodiments, the CMC-peptide conjugate is formed using carbodiimide chemistry to form an amide bond between a carboxymethyl group of CMC and an amino group (e.g., the N-terminal amino group) of the peptide. A general reaction scheme is shown below.

Scheme 1

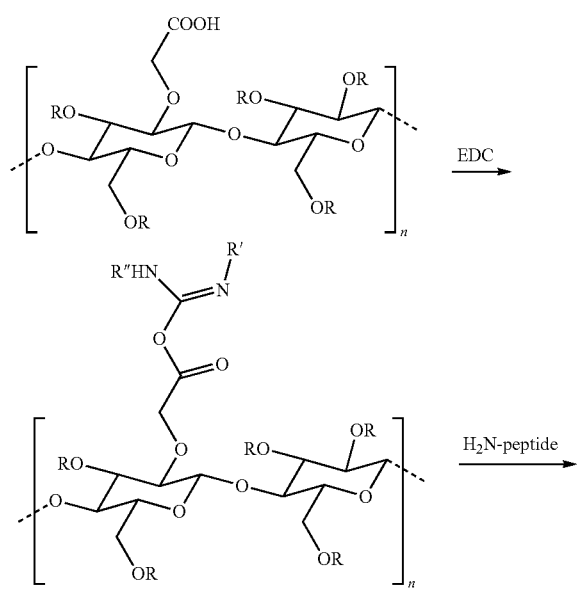

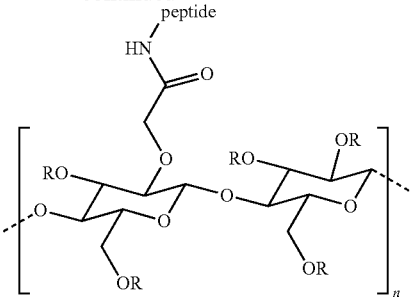

1-ethyl-(dimethylaminopropyl)carbodiimide (EDC), a water soluble carbodiimide, may be used to form an amide bond between a peptide and a carboxymethyl group on CMC. N-hydroxy-sulfosuccinimide (sulfo-NHS) may be included in the reaction to stabilize the reactive EDC-intermediate against hydrolysis. In some instances, the reaction is carried out in a buffer solution, such as a buffer solution in which the composition is soluble, such as a buffer solution in which CMC, CMC-peptide conjugate, and/or MC is soluble. For example, the reaction may be carried out in morpholinoethanesulfonic acid (MES) buffer. Following conjugation of the peptide to CMC, the resulting conjugate may be isolated from the reaction mixture by dialysis.

Formulations

In certain embodiments, the composition is formulated for administration to a target treatment site in a subject. For example, the composition may be formulated to facilitate administration to a cardiac tissue in a subject. In some instances, the composition is formulation to facilitate injection of the composition to the target treatment site in the subject. In certain cases, the composition is formulated to be injected, such as through a delivery lumen of a delivery catheter or a syringe.

As described above, after administration of the composition, the composition may increase in temperature due to absorption of heat from surrounding body tissue of the subject. In some cases, the body temperature of the subject is sufficient to cause the composition to increase in viscosity (e.g., transition from a liquid to a gel) as described above. The increase in viscosity (e.g., gelling) may give rise to a 3-dimensional network sufficient to provide structural and/or geometric support to a body tissue, such as a cardiac tissue (e.g., a cardiac tissue of an infarct region). In one approach, a syringe or catheter may be used to inject the composition in vivo. The composition may be injected directly to the treatment site, or may be allowed to partially pre-heat in the syringe in order to increase the viscosity of the composition prior to injection. In some instances, a pre-heated formulation may reduce the possibility that a less viscous composition may diffuse and/or migrate away from the tissue area of interest after injection. In addition to providing mechanical integrity for interstitial scaffolding, compositions with covalently attached peptides may enhance cell proliferation in MI damaged cardiac tissue.

In certain embodiments, the composition (e.g., a composition that includes MC:CMC-peptide conjugate) may be included in a formulation in an amount ranging from 1% to 50% (w/v), such as 1% to 45%, including from 1% to 40%, or 1% to 35%, or 1% to 30%, or 1% to 25%, or 1% to 20%, or 5% to 20%, or 5% to 15%, or 10% to 15% (w/v). In some instances, the composition is included in the formulation in an amount ranging from 10% to 15% (w/v), such as 12% (w/v). The formulation may also include a solution, such as a buffer or saline, and the like. In certain instances, the formulation includes one or more additional components, such as, but not limited to, an adjuvant, an excipient, a dye, a marker (e.g., a radiopaque marker), a drug, and the like, and combinations thereof.

Methods

Aspects of the present disclosure include a method for treating an individual having an injured tissue by administering to the individual a subject composition (i.e., a composition comprising (i) carboxymethylcellulose (CMC) conjugated to a subject ECM peptide (a CMC-peptide conjugate); and (ii) methylcellulose (MC)). The methods are useful for the repair and/or regeneration of injured mammalian tissue in vivo.

The terms "treatment", "treating", "treat" and the like are used herein to generally refer to obtaining a desired physiologic and/or pharmacologic effect. The effect can be therapeutic in terms of a partial stabilization, a complete stabilization, or a cure for an injury, a disease, and/or an adverse effect (e.g., symptom) attributable to an injury or disease. The term "treatment" therefore includes: (a) arresting and/or slowing the progression of an injury, disease, and/or symptom(s); and/or (b) relieving the injury, disease, and/or symptom(s) (i.e., causing regression of the disease and/or symptom(s), accelerating healing after an injury, facilitating healing after an injury when the injury would otherwise not heal, etc.).

Any tissue injury is suitable to be treated with a subjection composition. Non-limiting exemplary tissue injuries suitable for treatment with the compositions and methods described herein include: injury due to disease, injury due to infection, ischemic injury (e.g., chronic ischemic cardiomyopathy), re-perfusion injury, congestive heart failure, bone fractures, dental decay, inflammatory injury (e.g., due to placement of pace maker electrodes, due to arthritis, etc.), chemotherapy, radiation or thermal injury, injuries resulting from trauma (e.g. vascular damage due to stents and catheters), tissue hypertrophy, tissue hyperplasia, fibrosis, and myocardial infarction.

Any injured tissue is suitable to be treated with a subjection composition. Non-limiting exemplary tissues that can be targeted with the compositions and methods described herein include: cardiac, smooth muscle, skeletal muscle, neural, hepatic, renal, cartilage, ocular, vascular, dental, bone, and bone marrow.

Administration

The subject compositions may be administered by any convenient means known to one of ordinary skill in the art. Suitable routes of administration include direct injection or application to the injured tissue. Suitable routes also include injection or application to a site adjacent to the injured tissue. Administration may include parenteral administration (e.g., intravenous, intramuscular, or intraperitoneal injection), subcutaneous administration, administration into vascular spaces, and/or administration into joints (e.g., intra-articular injection). Additional routes of administration include intranasal, topical, vaginal, rectal, intrathecal, intraarterial, and intraocular routes.

In some cases, as a non-limiting example, cardiomyopathy may be treated by distributing a subject composition within the myocardium in a pattern about one or more chambers of the heart. Patterns of distribution of a subject composition within the myocardium may be used to treat localized conditions such as myocardial infarctions, overt aneurysm of the ventricular wall as typically forms in response to large transmural myocardial infarctions, and mitral regurgitation due to a noncompliant mitral valve. These techniques may also be used to treat localized conditions that may not yet have progressed to cardiomyopathy. For additional information, see U.S. patent applications US 20080065047 and 20080065046, both of which are hereby incorporated by reference in their entirety.

For example, the subject composition can be injected or implanted into the myocardium in patterns, which may be envisioned as shaped distributions of injection or implant sites (or both), or even more simply as one or more lines (including arcs) of injection or implant sites (or both). The pattern may be envisioned relative to the entire heart, to one or more ventricles of the heart, or to one or more atria of the heart to effect a global resizing and/or reshaping of the heart or one or more of its various chambers. In one suitable pattern, one or more lines may be envisioned that extend circumferentially about whole or part of one or more heart chambers such as the atria and ventricles. In the case of the left ventricle, for example, one or more such lines may be used, depending on the degree of enlargement of the left ventricle. The number of injection or implant sites per circumferential line depends on the size of the heart and location of the line, but may involve from, for example, two to eight sites or more, or five to seven sites or more.

In another example of a pattern, lines composed of multiple injection sites which lines extend longitudinally the whole distance or part of the distance from proximate the apex to proximate the base. Such may be referred to herein as global patterning or global treatment. In the case of the left ventricle, for example, two or more such lines may be used, depending on the degree of enlargement of the left ventricle. The number of injection or implant sites per longitudinal line can vary with the size of the heart and location of the line, but may involve from, for example, two to seven sites, and preferably from four to six sites. Where injections are used, the injections may be but need not necessarily be of uniform dose and spacing and depth within the myocardium. The injection sites may be in the middle of the myocardium, or closer to the endocardium or to the epicardium, as desired. The contraction direction of the cardiac muscle fibers, which typically varies with depth in the myocardium, may be taken into account in deciding on the depth of the injection.

Localized patterning may be used to treat a localized heart anomaly such as an aneurysm arising from a myocardial infract or a mitral valve annulus disorder resulting in mitral regurgitation, either on its own or as part of a global treatment. Mapping or imaging may be performed to identify the location of a localized heart anomaly. Where used along with a global treatment, the local pattern may separate from a general pattern.

Where injections are used to administer a composition of the present disclosure, the injections may be but need not necessarily be of uniform dose and spacing and depth within the myocardium. The injection sites may be in the middle of the myocardium, or closer to the endocardium or to the epicardium, as desired. While the examples above (regarding patterns) relate to the heart, similar strategies can be adapted and used on any injured tissue, as will be readily apparent to one of ordinary skill in the art.

The depth of injection via needle delivery may be controlled by standard surgical techniques well known to those skilled in the art (e.g., in the course of cardiac surgery). Different volumes of a subject composition, and different numbers, sizes, patterns, and/or lengths of injection needles may be used to suit a particular need. In one regard, a prior diagnostic analysis may be used to determine the extent of the condition, location of the condition, or various anatomical considerations of the patient (i.e., individual) which parameters set forth the volume and/or pattern of a subject composition or injection needle or injection needle array to use for delivery. A real time diagnostic approach may allow for stimulus or other effects to be monitored or mapped, such that the amount of a subject composition, or distance, direction, or number of needle deployment, is modified until the correct result is achieved. Therefore, for example, the needles of such embodiments may be retractable and advanceable through tissue so that different arrangements may be tried until the damaged region is mapped and characterized for appropriate injection. For additional information, see U.S. patent application US 2008/0069801, which is hereby incorporated by reference in its entirety.

It is to be appreciated that while needle or "end-hole" injection delivery catheters may be used to inject the subject compositions, more complex "needle" injection devices may also be used, such as, for example, using screw needles with multiple ports along the screw shank; using needle devices with multiple adjacent needles; using multiple-barrel needle assemblies; etc.

Single injections of agent with a single lumen catheter are suitable in some cases. However, a multiple-lumen catheter may be used if desired to deliver a multiple-part agent (e.g., a first solution containing the CMC-peptide component, and a second solution containing the MC component; a first solution containing the CMC-peptide conjugate and MC, and a second solution containing an additional component to be administered). The parts of a multiple-part formulation may be provided contemporaneously or serially, depending on the properties of the formulation. Multiple single lumen catheters may be used if desired. The formulation and catheter or catheters may be provided in kit form, or as individual components of an injection system.

Multiple needles may be employed in a spaced fashion over a region for delivery, allowing for the injection and subsequent diffusion or other transport mechanisms in the tissue to close the gaps between scaffolds from discrete injection sites and cover the region. It is also to be appreciated that other delivery systems may be beneficially provided along a larger region of tissue generally achievable by traditional "end-hole" injection approaches. For example, subjection compositions may be injected along a substantial portion of a ventricle wall, both wide and deep.

For the purpose of further illustration, other more specific examples of delivery devices and methods that may be modified are variously disclosed in one or more of the following documents: U.S. patent application 20080069801, U.S. Pat. Nos. 5,722,403; 5,797,903; 5,885,278; 5,938,660; 5,971,983; 6,012,457; 6,024,740; 6,071,279; 6,117,101; 6,164,283; 6,214,002; 6,241,754; 6,245,064; 6,254,599; 6,305,378; 6,371,955; 6,383,151; 6,416,511; 6,471,697; 6,500,174; 6,502,576; 6,514,249; 6,522,930; 6,527,769; and 6,547,788; and US Patent Application Publication No. 2005/0271631, all of which are hereby incorporated by reference in their entirety. To the extent that these references variously relate to ablating tissue or other therapeutic uses other than cell or polymer scaffolding delivery or treating the conditions contemplated herein, certain aspects of the respective catheter systems and therapy may be modified or otherwise per the intent and objects of this disclosure as appropriate to one of ordinary skill. For example, where ablation devices are disclosed, various related elements such as ablation electrodes, leads, transducers, optical assemblies, or the like, can be replaced with suitable elements for injecting the subject compositions described herein.

The subject compositions described herein (i.e., a composition comprising a CMC-peptide conjugate and MC) can be administered to an individual alone, or in conjunction with other therapies suitable for treatment of the particular injury. For example, a subject composition may be administered in conjunction with angioplasty to facilitate the repair of injured cardiac tissue. As an illustrative example, in some embodiments, a subject composition can be administered prior to angioplasty, contemporaneous with angioplasty, or subsequent to angioplasty.

The amount of targeted EMD peptide required to facilitate tissue repair and/or regeneration is defined as a "therapeutically effective dose." The dosage schedule (e.g., an injection schedule, which may be a single injection or may be multiple injections) and amounts effective for a particular use, i.e., the "dosing regimen," will depend upon a variety of factors, including the tissue being treated, the type of injury, components of the subject composition, the individual's physical status, the route of administration, and the desired end-point sought to be achieved, all of which can be taken into account. Single or multiple administrations of the compositions may be administered depending on the dosage and frequency as required and tolerated by the individual. Typically, a pharmaceutical composition of the invention is administered as a single, or multiple therapeutically effective dose over a single day, several days, or weeks, or by daily or weekly administrations (e.g., injections). In some cases of chronic injury, such as intractable angina, multiple doses separated by months may be required due to the changing pathophysiological state. In any event, dosage and administration schedule should provide for a sufficient quantity of the subjection composition to effectively treat the patient (as defined above).

In some embodiments, a therapeutically effective dose of a subject composition may be in a range from about 0.05 µg to about 500 µg, or about 5 µg to about 400 µg, or about 10 µg to about 300 µg, or about 25 µg to about 250 µg, or about 40 µg to about 100 µg, or about 50 µg of a subject composition per dose (e.g., per injections). In some embodiments, the amount of a subject composition that is administered is based on body weight. In some embodiments, the amount of a subject composition that is administered is from about 0.05 ng to about 500 ng, or about 5 ng to about 400 ng, or about 10 ng to about 300 ng, or about 25 ng to about 250 ng, or about 40 ng to about 100 ng, or about 50 ng per kg of body weight. In some embodiments, the dose is based on patient surface area and/or the surface are of the injury. For example, in some embodiments, a subject composition may be administered in a dose range from about 50 mg to about 400 mg/m$^2$ of surface area, or about 100 mg to about 300 mg/m$^2$ of surface area, or about 150 mg to about 250 mg/m$^2$ of surface area. In some embodiments, the dose administered is about 250 mg/m$^2$ of surface area. In some embodiments, the dose is administered as a single cycle, while in other embodiments, multiple cycles are administered. The exact dose and schedule of administration will depend on a variety of factors as discussed herein, and is well within the skill of a medical professional that may be treating the individual.

Kits

Also provided are kits that include the compositions described herein and which find use in the methods described above. In certain embodiments, the kit includes a sterile container that includes a composition as described herein. By "sterile" is meant that there are substantially no microbes (such as fungi, bacteria, viruses, spore forms, etc.).

For example, the container may be configured to maintain the sterility of the composition contained within the container.

In certain embodiments, the container includes a chamber configured to contain the composition, such as a MC:CMC-peptide conjugate composition as described above. The composition may be dispensed from the chamber according to the methods described above.

In certain embodiments, the container includes two separate chambers and is configured to maintain the components of the composition in separate chambers during storage and until use. For example, the container may include a first chamber that includes a CMC-peptide conjugate composition and a second chamber that includes a MC composition. The first and second chambers may be separate chambers that do not allow the CMC-peptide conjugate composition and the MC composition to contact each other until use. In some cases, the container includes a nozzle. The nozzle may be in fluid communication with the two chambers of the container. For example, the nozzle may be in fluid communication with the first and second chambers as described above. In some embodiments, the container is configured to dispense the CMC-peptide conjugate composition and the MC composition through a single nozzle. In these embodiments, the container may be configured to mix the CMC-peptide conjugate and the MC compositions as the CMC-peptide conjugate and MC compositions are dispensed from the container through the nozzle. Embodiments of the container that include a nozzle as described above may facilitate the in situ mixture and application of the MC:CMC-peptide conjugate composition to a target treatment site.

For example, in one approach, a dual chamber syringe converging into a single lumen injection needle may be used to inject the mixed components of the composition to gel in-vivo. Prior to injection, for example, a T-type adapter may be attached to the syringe and configured to provide mixing of the components and allow the composition to enter the lumen of the injection needle to be injected into the tissue of interest (e.g., cardiac tissue of interest). In another approach, the CMC-peptide conjugate and MC compositions may be pre-mixed in an external mixing chamber, and aspirated into a single lumen syringe from which it may then be injected into the target tissue of interest (e.g., cardiac tissue of interest).

Single injections of the composition with a single lumen catheter are suitable for compositions that are designed not to clog a single lumen, because of the speed of injection, lessening of trauma, and relative ease of injection. However, a multiple-lumen catheter may be used if desired to deliver a multiple-part composition such as a first solution containing a CMC-peptide conjugate and a second solution containing a MC composition. The parts of a multiple-part formulation may be provided contemporaneously or serially, depending on the properties of the formulation. Multiple single lumen catheters may be used if desired. The formulation and catheter or catheters may be provided in kit form, or as individual components of an injection system.

Embodiments of the kit for applying a composition may also include other types of devices suitably adapted for administering the composition to the subject. For example, the device may include a pressurized container. The pressurized container may include one or more chambers as described above (e.g., a first chamber and a second chamber). The pressurized container may be configured to maintain the contents of the one or more chambers at a pressure greater than standard atmospheric pressure. In some instances, the pressurized container includes a valve, and may be configured to dispense the contents of the one or more chambers when the valve is in an open position, thereby allowing the pressurized contents of the container to be released from the container.

In addition to the above components, the kits may further include instructions for practicing the methods. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, the present disclosure has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

The materials and methods below were used for Examples 1-4:

Peptide Conjugation

To enhance the interaction of cells to the polymer surface, extracellular matrix (ECM)-derived peptides were conjugated to polymers of carboxymethylcellulose (CMC), a derivative of methylcellulose (MC) where carboxymethyl groups have replaced some of the of the hydroxyl groups of the glucopyranose monomers of the polymer backbone. (CMC, 419273, Sigma-Aldrich, St. Louis, Mo.) One advantage to using CMC is the relative ease in covalently attaching a cell adhesion-promoting ECM-derived functional moiety to the polymer.

The peptides were synthesized and purified by AI Biotech (Richmond, Va.). GRGDSPASSPISC (RGD) (SEQ ID NO: 1) and GEFYFDLRLKGDKY (SEQ ID NO: 2) (HepIII) were each conjugated to carboxymethylcellulose (Sigma-Aldrich, St. Louis, Mo.) using a conjugation technique that utilizes carbodiimide chemistry (Rowley et al, Biomaterials. 1999 January; 20(1):45-53; and Ogushi et al, Journal of Bioscience and Bioengineering. 2007; 104(1):30-3; both of which are hereby incorporated by reference in their entirety). In brief, EDC along with sulfo-NHS (Pierce, Rockford Ill.) was added to the carboxymethylcellulose, which was dissolved in MES buffer solution, to activate the carboxylic acid groups within the polymer chain. The peptide was then added and allowed to react at room temperature for about 2 days. Afterwards, the polymer solution was dialyzed against pyrogen-free water to remove any unreacted peptide and lyophilized. To approximate the conjugation efficiency of peptide to the polymer, a tryptophan-containing peptide, WQPPRARI (SEQ ID NO: 3), was used to allow for determination of the amount of peptide incorporated into the polymer using UV-vis spectrophotometery (Larsen et al, Biomaterials. 2007; 28(24):3537-48, which is hereby incorporated by reference in its entirety).

In Vitro Cell Attachment

An optimal composition of MC:CMC-peptide for cell attachment was determined by examining a range of MC:CMC-peptide mixtures. 12% (w/v) polymer solutions were prepared by mixing the peptide-modified CMC with methylcellulose (MC, M7027, Sigma-Aldrich, St. Louis, Mo.) at various ratios. Preparation of polymer-coated dishes and culturing of the cells were done as previously described (Wand et al, Cardiovasc Res. 2008 Feb. 1; 77(3):515-24, which is hereby incorporated by reference in its entirety). We added 500 µL of polymer solution to each tissue culture dish. To form the gel, the dishes were incubated at 37° C. for at least 1 hour. Human umbilical vein endothelial cells (HUVECs, Lonza, Basel, Switzerland) were cultured on the polymer-coated dishes. After 2 days, the dishes were checked using phase-contrast microscopy (Nikon Eclipse TE300, Nikon Instruments Inc., Melville, N.Y.) for adherent cells.

Rheology Studies

Rheology measurements (Advanced Rheometer AR2000, TA Instruments, New Castle, Del.) were done on MC:CMC, MC:CMC-RGD, and MC:CMC-HepIII co-polymers mixed at a 5:1 ratio. The elastic modulus and viscous modulus were determined for temperatures ranging from 20-40° C., with 1° C. increments. The equilibration time was set at 1 min. and the frequency was set at 1 Hz. The gelling temperature was defined as the point of intersection between the plot for the elastic modulus and the plot for the viscous modulus. Measurements were done in triplicate.

Chronic Myocardial Infarction Model and Echocardiography

All surgical procedures were approved by the Committee for Animal Research of the University of California San Francisco (San Francisco, Calif.). Female Sprague-Dawley rats (225-250 g) were anesthetized with isoflurane. The chest was opened by a median sternotomy, and a single stitch of 7-0 Ticron suture (United States Surgical division of Tyco Healthcare, Norwalk, Conn.) was introduced around the left anterior descending (LAD) coronary artery and tightened to occlude for 30 min. before re-perfusing the vessel (Yu et al, J Thorac Cardiovasc Surg. 2009 Jan. 1, 2009; 137(1):180-7; Christman et a, J Am Coll Cardiol. 2004; 44(3):654-60; Christman et al, Tissue Eng. 2004; 10(3-4):403-9; Huang et al, Tissue Eng. 2005; 11(11-12):1860-6; Sievers et al, Magn Reson Med. 1989; 10:172-81; and Yu et al, Biomaterials. 2009; 30(5):751-6; which are hereby incorporated by reference in their entirety). Cardiac monitoring during the LAD occlusion confirmed the presence of myocardial injury as indicated by ST-elevation. The chest was then closed and the animal was allowed to recover for 5 weeks in order to allow for a LV aneurysm to fully develop. Transthoracic echocardiography was performed 5 weeks post-MI and 5 weeks post-treatment as previously described (Yu et al, J Thorac Cardiovasc Surg. 2009 Jan. 1, 2009; 137(1):180-7; and Litwin et al, Circulation. 1994; 89:345-54; which are hereby incorporated by reference in their entirety).

Polymer Injection

Five weeks post-MI and prior to treatment, we verified the LV aneurysmal formation and compromised LV function via echocardiography. The rats were randomized into MC:CMC, MC:CMC-RGD, MC:CMC-HepIII, or phosphate-buffered saline (PBS) control groups (N=8-9 rats/group). Using a closed chest echocardiography-guided injection technique (Springer et al, American Journal of Physiology—Heart and Circulatory Physiology. Sep. 1, 2005; 289(3):H1307-H14; which is hereby incorporated by reference in its entirety), 100 µL of polymer or PBS solution was injected into the infracted LV region of each heart, using a 1 mL syringe system and a 25-gauge needle.

Histology

Five weeks post-treatment (10 weeks post-MI), the rats were euthanized and their hearts were harvested, rinsed in cold saline, blotted-dry and fresh frozen in Tissue Tek O.C.T. freezing medium (Sakura Finetek, Torrance, Calif.). The hearts were sectioned into 10 µm slices. Sequential slides spanning the LV region were stained with Masson's trichrome stain and were used for morphological assessment of the infarct size as previously described (Christman et al, J Am Coll Cardiol. 2004; 44(3):654-60). Angiogenesis, arteriogenesis, and the number of cardiac cells within the infarct region were examined by immunohistochemical (IHC) staining with mouse monoclonal anti-CD31 (BD Biosciences Pharmingen, San Diego, Calif.) to visualize capillaries, mouse monoclonal anti-α-smooth muscle actin (Sigma, St. Louis, Mo.) to detect arterioles (Virag et al, Am J Pathol. 2003 Dec. 1, 2003; 163(6):2433-40; which is hereby incorporated by reference in its entirety), and mouse monoclonal anti-rat cardiac α-myosin heavy chain (Panorama Research Institute, Mountain View, Calif.) to detect the cardiac cells. The staining assay was performed using mouse-on-rat HRP-polymer (Biocare Medical, Concord, Calif.) on slides that were sequential to the slides stained with trichrome. Capillaries in the infarct region were identified as a single layer of CD31-positive cells with flattened morphology. Vessel density, cardiac cell density, and nuclei density was calculated on the basis of 5 high magnification fields per section that spanned the infarct and averaged among 5 sections for each sample. Arterioles within or bordering the infarct were identified as staining positive for α-smooth muscle actin and as having a visible lumen with a diameter between 10 and 100 μm (Yu et al, J Thorac Cardiovasc Surg. 2009 Jan. 1, 2009; 137(1):180-7; and Christman et a, J Am Coll Cardiol. 2004; 44(3):654-60). Arteriole density was calculated as the average number of arterioles in the total infarct area, out of 5 representative slides per sample. Cardiac cell density and overall cell density were calculated on the basis of 5 high magnification fields per section. Cardiac cell number was determined by counting nuclei, counterstained with hematoxylin, that were surrounded by positive stains for rat cardiac α-myosin heavy chain.

Statistics

Echocardiography data and histology data are presented as mean±standard deviation. Rheology measurements are presented as mean±standard error from the mean. Differences between echocardiography measurements before and after treatment were compared, using the paired t test. Differences in the echocardiography measurements, infarct size, vessel counts, cardiac cell counts, and nuclei counts across treatment groups were compared, using repeated one-way analysis of variance (ANOVA) with Holm's adjustment. Significance was accepted at $P<0.05$.

Example 1

Determination of the Optimal Composition of MC:CMC-Peptide for Cell Attachment

The carbodiimide conjugation method resulted in ~3.6 mg peptide per g of CMC polymer as determined by measuring the absorbance at 280 nm. We tested MC:CMC-peptide (w:w) ratios of 1:0, 10:1, 5:1, and 3:1 for in vitro HUVEC attachment. HUVEC attachment was only observed for the 5:1 MC:CMC-peptide ratio (~0.6 mg peptide per g MC:CMC).

Example 2

Intrinsic Properties of MC:CMC Compositions

Figure 1:
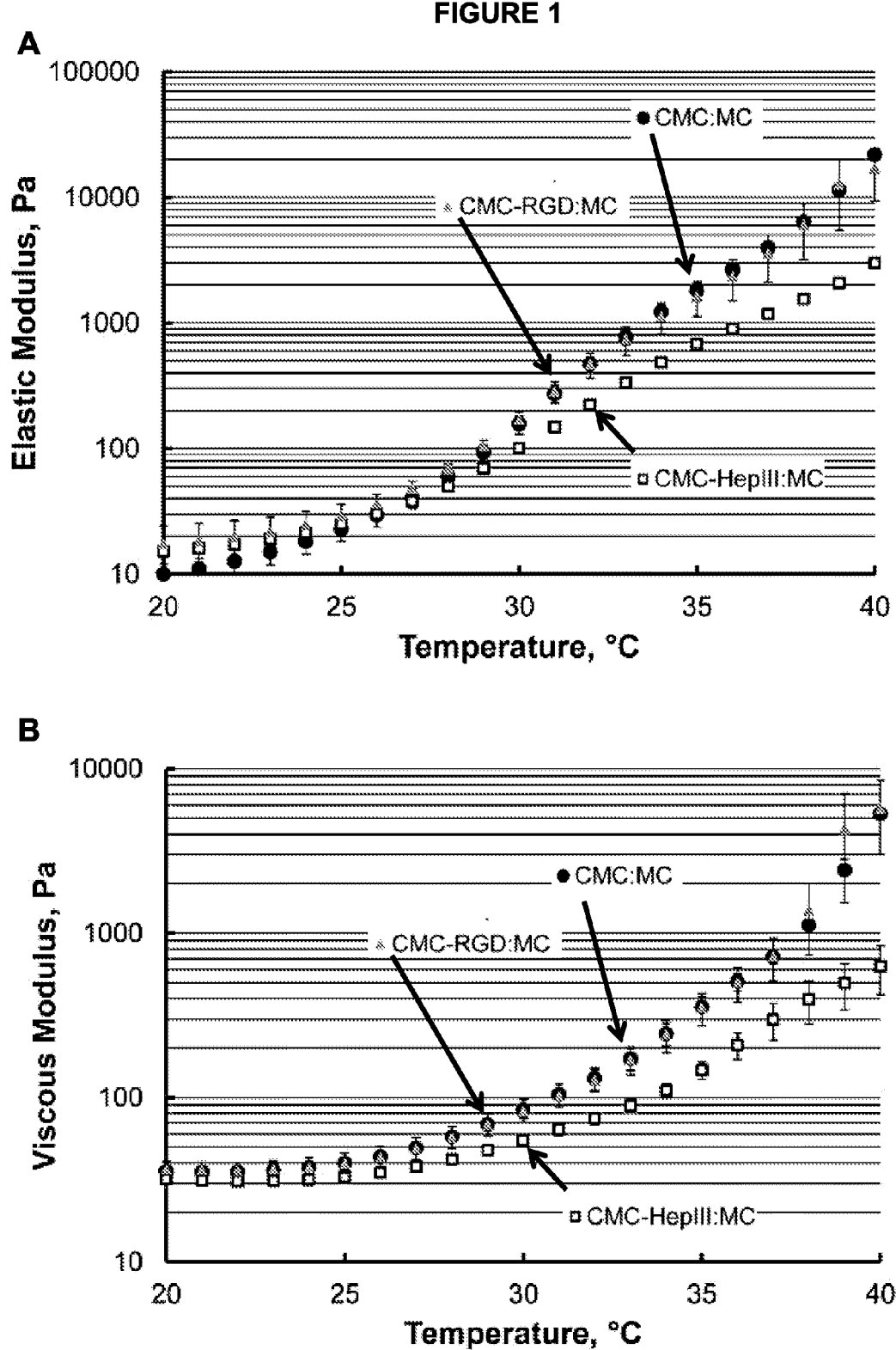

The viscoelastic properties and the gelling temperature of the MC:CMC polymer blend where determined using a rheometer. Since the in vitro cell attachment assay showed that the best MC:CMC ratio was 5:1. Our rheological studies were done with the unmodified and the peptide-conjugated MC:CMC polymer blends at that ratio. We found that RGD conjugation did not significantly alter the viscoelastic properties of the polymer when compared to the unconjugated polymer (FIG. 1). However, interestingly, HepIII conjugation did alter the viscoelastic properties of the polymer, resulting in decreased stiffness and viscosity of the polymer as the temperature increased. The gelling temperature (Table 1), which is defined as the temperature at which the plots for the viscous modulus and elastic modulus intersect, was determined. It would appear that conjugation of the peptide to the polymer acted to slightly decrease the gelling temperature.

TABLE 1

Effect of peptide modification on the gelling temperature of 5:1 MC:CMC polymer blends.

| Polymer | Gelling temperature (° C.) |
| --- | --- |
| MC:CMC | 27.67 ± 0.1112 |
| MC:CMC-RGD | 26.75 ± 0.4954 |
| MC:CMC-HepIII | 26.85 ± 0.6256 |

FIG. 1 presents a rheological analysis of the unmodified and peptide-modified 5:1 MC:CMC polymer blends. The viscoelastic properties of the polymer blends were measured at a temperature range of 20° C. to 40° C. (a) Plot of the elastic modulus as a function of temperature. (b) Plot of the viscous modulus as a function of temperature.

Example 3

Effect on LV Function

The functional effects of treatment with MC:CMC, MC:CMC-RGD, MC:CMC-HepIII were investigated by echocardiography (27, 33) at baseline (5 weeks post-MI and before treatment) and 5 weeks post-treatment (FIG. 2). PBS was used as a negative control. All of the rats that underwent ischemia/reperfusion surgery exhibited wall thinning of the LV infarct wall and compromised LV function prior to treatment.

The baseline data indicated that there were no statistically significant differences between the treatment groups in the parameters measured. Echocardiography done 5 weeks post-treatment (10 weeks post-MI) showed statistically significant improvement of LV ejection fraction and the fractional area change (FAC) (Nozawa et al, Braz J Med Biol Res. 2006; 39:687-95; which is hereby incorporated by reference in its entirety). in animals treated with either MC:CMC-RGD or MC:CMC-HepIII compared to baseline measurements (FIG. 2, Panels a and b). The ejection fraction for the MC:CMC-RGD treatment group significantly increased from 34.2±1.91% to 42.9±8.29% and the MC:CMC-HepIII treatment group significantly increased from 36.9±2.18% to 43.0±6.25%. The FAC for the MC:CMC-RGD treatment group significantly increased from 36.0±2.44% to 44.0±9.26% and the MC:CMC-HepIII treatment group significantly increased from 36.9±2.60% to 45.6±9.63%.

For animals treated with MC:CMC, the LV ejection fraction and FAC remained essentially unchanged relative to measurements determined at baseline. The ejection fraction and FAC for the MC:CMC treatment group before treatment were 35.1±3.49% and 37.3±2.80%, respectively, and, 5 weeks post-treatment were 34.9±6.81% and 38.6±9.02%, respectively.

There was statistically significant worsening of LV function in the animals treated with PBS. Both the ejection fraction and the FAC were lower at 5 weeks post-treatment. The ejection fraction and FAC went from 34.7±2.87% and 37.5±2.60%, respectively, to 31.0±3.65% and 33.8±4.60%, respectively.

An increase in the MI wall thickness was observed (FIG. 2, Panels c-f) in animals treated with MC:CMC, MC:CMC-RGD, or MC:CMC-HepIII. The 3 polymer treatment groups showed statistically significant higher systolic MI wall thickness at 5 weeks post-treatment compared to baseline. The PBS group showed statistically significant thinning of both the diastolic MI wall thickness and the systolic MI wall thickness compared to baseline.

Furthermore, we found that diastolic and systolic volumes for rats treated with MC:CMC-RGD or MC:CMC-HepIII significantly decreased at 5 weeks post-treatment. The diastolic and systolic volumes for rats treated with MC:CMC exhibited no statistical difference between measurements at baseline and measurements at 5 weeks post-treatment.

Comparison between the treatment groups at 5 weeks post-treatment showed that both MC:CMC-RGD and MC:CMC-HepIII exhibited statistically significant better ejection fraction, FAC, diastolic volume, and systolic volume compared to the PBS negative control group. In addition, MC:CMC-HepIII-treated rats had statistically significant smaller diastolic and systolic volumes compare to the MC:CMC-treated rats. All of the polymer treatment groups showed statistically significant thicker wall thickness at 5 weeks post-treatment relative to the PBS negative control group. There was no statistical difference between the MC:CMC-RGD treatment group and the MC:CMC-HepIII treatment group.

FIG. 2 presents echocardiography data. Analysis of the ejection fraction (a) and the fractional area change (FAC) (b) revealed that the MC:CMC-RGD and the MC:CMC-HepIII treatment groups resulted in improved cardiac function, while the PBS treatment group resulted in deterioration of cardiac function, compared to the baseline at 5 weeks post-MI, pre-treatment. Assessment of the infarct wall thickness at diastole ((c) and (e)) and infarct wall thickness at systole ((d) and (f)) showed that polymer treatment thickened the infarct wall, while the PBS treated rats exhibited continued thinning of the infarct wall. *$P<0.05$.

Example 4

Effect on MI Size and Angiogenesis

To determine the infarct size, heart sections were treated with Masson's trichrome stain. There was a statistically significant reduction in infarct size in the hearts of animals treated with either MC:CMC-RGD or MC:CMC-HepIII when compared to the PBS negative control (FIG. 3, panel e). We observed no statistical difference between the MC:CMC-RGD group and the MC:CMC-HepIII group. At the same time, we observed a higher density of cardiomyocytes within the infarct region of the MC:CMC-RGD and the MC:CMC-HepIII treatment groups compared to the PBS negative control (FIG. 4). The overall cell density among the different treatment groups was similar. Furthermore, we observed higher levels of angiogenesis (FIG. 3, Panels a-d, f, and g) within the infarct region of the MC:CMC-RGD and the MC:CMC-HepIII treatment groups.

Determination of the arteriole density within the infarct region of the heart (FIG. 3, panel f) in rats treated with MC:CMC-RGD ($32\pm12$ arterioles/mm$^2$) or MC:CMC-HepIII ($28\pm10$ arterioles/mm$^2$) showed statistically significantly higher arteriole density when compared to rats treated with PBS ($17\pm3$ arterioles/mm$^2$) or with MC:CMC ($18\pm4$ arterioles/mm$^2$). There was no statistical difference in arteriole density between the PBS negative control and MC:CMC treatment group and between the MC:CMC-RGD treatment group and MC:CMC-HepIII treatment group.

Assessment of capillary density in the infarct region (FIG. 3, panel g), showed that rats treated with MC:CMC ($317\pm96$ capillaries/mm$^2$), MC:CMC-RGD ($472\pm146$ capillaries/mm$^2$), or MC:CMC-HepIII ($424\pm56$ capillaries/mm$^2$) had statistically significantly higher capillary density compared to the PBS negative control ($195\pm39$ capillaries/mm$^2$). Furthermore, we found that rats treated with MC:CMC-RGD or MC:CMC-HepIII also had statistically significantly higher capillary density compared to rats treated with MC:CMC. There was no statistical difference between the MC:CMC-RGD treatment group and the MC:CMC-HepIII treatment group.

FIG. 3 presents an immunohistological assessment of the hearts. Representative images of staining for capillaries and arterioles within the infarct region of hearts from rats treated with (a) PBS, (b) unmodified MC:CMC, (c) MC:CMC-HepIII, or (d) MC:CMC-RGD. Scale bar represents 325 μm. (e) Infarct size measurements showed statistically significant decrease MI size in rats treated with either MC:CMC-RGD or MC:CMC-HepIII. *$P<0.01$ vs. PBS. (f) Arteriole staining showed statistically significantly higher arteriole density for rats treated with either MC:CMC-RGD or MC:CMC-HepIII. *$P<0.05$ vs. PBS, # $P<0.05$ vs unmodified MC:CMC. (g) Capillary staining showed statistically significantly higher capillary density for rats treated with either MC:CMC-RGD or MC:CMC-HepIII. *$P<0.05$ vs. PBS, # $P<0.05$ vs. unmodified MC:CMC.

FIG. 4 presents an assessment of cardiomyocytes within the MI region. (a) Representative images of immunofluorescent staining for cardiac cells. We used mouse anti-rat cardiac α-myosin heavy chain and goat anti-mouse IgG$_{2b}$-Alexa Fluor 488. The magnification is at 40×. The scale bar represents 1.64 μm. (b) Analysis of heart sections stained immunohistochemically for mouse anti-rat cardiac α-myosin heavy chain showed statistically significantly higher cardiac cell density for rats treated with either MC:CMC-RGD or MC:CMC-HepIII. *$P<0.05$ vs. PBS.

Discussion

The studies presented here demonstrate that immobilization of ECM-derived peptides onto a thermo-reversible polymer greatly enhanced the repair process in a chronic rodent model of ischemic cardiomyopathy. The addition of relevant functional groups from either fibronectin or Type IV collagen facilitated the thermo-reversible MC:CMC polymer mixture to promote neovascularization, decrease MI size, reshape the aneurismal LV wall, and improve LV function in a chronic rat model of ischemic cardiomyopathy. The advantage to using thermo-reversible polymers was that, unlike alginate or fibrin glue, these polymers did not require additional mixing with another agent to induce gelation. Thus, the agents used here are more amenable to a percutaneous catheter-based form of administration. As a result, we were able to utilize a minimally invasive method of injection of polymer into the infarct region of the rats.

Although peptide conjugation to the polymer tended to slightly decrease the gelling temperature, this difference did not cause any additional difficulties when administering the polymers to the animals. From our rheological studies, we determined that the unconjugated and peptide-conjugated MC:CMC polymer blends that we injected into the rats had an elastic modulus on the order of 1 kPa at 37° C. We observed a maintenance of LV function with the MC:CMC treatment group, while observing a significant restoration of LV geometry and improvement of LV function in the MC:CMC-peptide-treated rats.

Conjugation of the MC:CMC polymer blends with peptides demonstrated several beneficial effects, including increased wall thickness, improvement of LV function, angiogenesis, and a decrease in MI size compared to both PBS and MC:CMC treatment groups. We also found a higher concentration of cardiomyocytes within the infarct region among the rats treated with the peptide-conjugated polymer. These results suggest that, in vivo, the peptides may be facilitating myocardial repair by interacting with the pre-existing myocardial ECM and cells within the MI region.

The results of this study demonstrate the ability to synthesize a bioactive polymer that can be used to repair chronic ischemic cardiomyopathy. The strategy of using a polymer to augment the LV wall leading to restoration of LV geometry and improved LV function combined with functional ECM groups to enhance a regenerative process presents a new strategy for the repair and regeneration of chronically injured myocardium.

The preceding merely illustrates the principles of the disclosure. All statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, e.g., any elements developed that perform the same function, regardless of structure. The scope of the present disclosure, therefore, is not intended to be limited to the exemplary embodiments shown and described herein. Rather, the scope and spirit of present disclosure is embodied by the appended claims.

That which is claimed is:

1. A composition comprising:
   a carboxymethylcellulose (CMC) conjugated to an extracellular matrix (ECM) peptide selected from the group consisting of a RGD peptide, a HepI peptide, a HepIII peptide, a FC/HV peptide, SEQ ID NO: 5, SEQ ID NO: 6, SEQ ID NO: 7, SEQ ID NO: 8, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 18, SEQ ID NO: 20, SEQ ID NO: 21, SEQ ID NO: 22, SEQ ID NO: 23, SEQ ID NO: 24, SEQ ID NO: 27, SEQ ID NO: 29, SEQ ID NO: 30, SEQ ID NO: 31, SEQ ID NO: 32 and SEQ ID NO: 33; and
   a methylcellulose (MC).

2. The composition of claim 1, wherein the CMC is directly bound to the ECM peptide to form a CMC-peptide conjugate.

3. The composition of claim 2, wherein the CMC-peptide conjugate is of the formula:

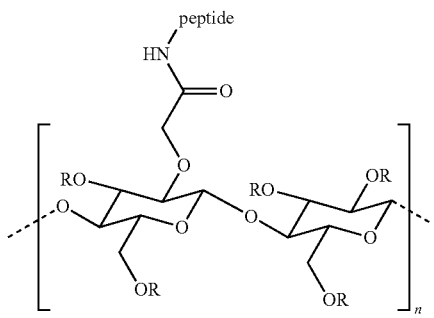

wherein R is H or —$CH_2COOH$.

4. The composition of claim 1, wherein the ECM peptide has a length ranging from 5 amino acid residues to 100 amino acid residues.

5. The composition of claim 4, wherein the ECM peptide is an RGD peptide (SEQ ID NO: 1) or a HepIII peptide (SEQ ID NO: 2).

6. The composition of claim 1, wherein the MC:CMC-peptide conjugate ratio (w/w) ranges from 1:1 to 10:1.

7. The composition of claim 6, wherein the MC:CMC-peptide conjugate ratio is 5:1.

8. A method for treating a subject having an injured tissue, the method comprising:
administering to injured tissue of the individual an effective amount of a composition comprising:
a carboxymethylcellulose (CMC) conjugated to an extracellular matrix (ECM) peptide selected from the group consisting of a RGD peptide, a HepI peptide, a HepIII peptide, a FC/HV peptide, SEQ ID NO: 5, SEQ ID NO: 6, SEQ ID NO: 7, SEQ ID NO: 8, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 18, SEQ ID NO: 20, SEQ ID NO: 21, SEQ ID NO: 22, SEQ ID NO: 23, SEQ ID NO: 24, SEQ ID NO: 27, SEQ ID NO: 29, SEQ ID NO: 30, SEQ ID NO: 31, SEQ ID NO: 32 and SEQ ID NO: 33; and
a methylcellulose (MC).

9. The method of claim 8, wherein the administering comprises injecting the composition at a site of injury in the subject.

10. The method of claim 8, wherein the injured tissue comprises a cardiac tissue.

11. The method of claim 8, wherein the ECM peptide is an RGD peptide (SEQ ID NO: 1) or a HepIII peptide (SEQ ID NO: 2).

12. The method of claim 8, wherein the MC:CMC-peptide conjugate ratio (w/w) ranges from 1:1 to 10:1.

13. The method of claim 12, wherein the MC:CMC-peptide conjugate ratio (w/w) is 5:1.

14. A kit comprising:
a sterile container comprising a composition, wherein the composition comprises:
a carboxymethylcellulose (CMC) conjugated to an extracellular matrix (ECM) peptide selected from the group consisting of a RGD peptide, a HepI peptide, a HepIII peptide, a FC/HV peptide, SEQ ID NO: 5, SEQ ID NO: 6, SEQ ID NO: 7, SEQ ID NO: 8, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 18, SEQ ID NO: 20, SEQ ID NO: 21, SEQ ID NO: 22, SEQ ID NO: 23, SEQ ID NO: 24, SEQ ID NO: 27, SEQ ID NO: 29, SEQ ID NO: 30, SEQ ID NO: 31, SEQ ID NO: 32 and SEQ ID NO: 33; and
a methylcellulose (MC).

15. The kit of claim 14, wherein the sterile container comprises a syringe.

16. The kit of claim 14, wherein the sterile container comprises a first chamber that includes a CMC-peptide conjugate composition, and a second chamber that includes a MC composition, wherein the compositions in the first and second chambers are separated from each other until use.

17. The composition of claim 1, wherein the RGD peptide is selected from the group consisting of RGD, GRGDS (SEQ ID NO: 14), RGDV (SEQ ID NO:15), RGDS (SEQ ID NO: 19), RGDF (SEQ ID NO: 20), GRGDY (SEQ ID NO: 25), GRGDSP (SEQ ID NO: 26), GGGGRGDSP (SEQ ID NO: 28) and GGGGRGDY (SEQ ID NO: 29).

18. A composition comprising:
a carboxymethylcellulose (CMC) conjugated to an extracellular matrix (ECM) peptide selected from the group consisting of a RGD peptide, a HepI peptide, a HepIII peptide, a FC/HV peptide, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20. SEQ ID NO: 21. SEQ ID NO: 22. SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33; and
a methylcellulose (MC).

19. The composition of claim 1, wherein the ratio of MC:CMC-peptide conjugate is configured to facilitate cell attachment.

* * * * *

```
                        SEQUENCE LISTING

<160> NUMBER OF SEQ ID NOS: 33

<210> SEQ ID NO 1
<211> LENGTH: 13
<212> TYPE: PRT
<213> ORGANISM: Artificial Sequence
<220> FEATURE:
<223> OTHER INFORMATION: synthetic polypeptide sequence

<400> SEQUENCE: 1

Gly Arg Gly Asp Ser Pro Ala Ser Ser Pro Ile Ser Cys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: synthetic polypeptide sequence

<400> SEQUENCE: 2

Gly Glu Phe Tyr Phe Asp Leu Arg Leu Lys Gly Asp Lys Tyr
1               5                   10

<210> SEQ ID NO 3
<211> LENGTH: 8
<212> TYPE: PRT
<213> ORGANISM: Artificial Sequence
<220> FEATURE:
<223> OTHER INFORMATION: synthetic polypeptide sequence

<400> SEQUENCE: 3

Trp Gln Pro Pro Arg Ala Arg Ile
1               5

<210> SEQ ID NO 4
<211> LENGTH: 13
<212> TYPE: PRT
<213> ORGANISM: Artificial Sequence
<220> FEATURE:
<223> OTHER INFORMATION: synthetic polypeptide sequence

<400> SEQUENCE: 4

Thr Ala Gly Ser Cys Leu Arg Lys Phe Ser Thr Met Tyr
1               5                   10

<210> SEQ ID NO 5
<211> LENGTH: 6
<212> TYPE: PRT
<213> ORGANISM: Artificial Sequence
<220> FEATURE:
<223> OTHER INFORMATION: synthetic polypeptide sequence
```

```
<400> SEQUENCE: 5

Val Gly Val Ala Pro Gly
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic polypeptide sequence

<400> SEQUENCE: 6

Leu Gly Thr Ile Pro Gly
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic polypeptide sequence

<400> SEQUENCE: 7

Tyr Ile Gly Ser Arg
1               5

<210> SEQ ID NO 8
<211> LENGTH: 12
<212> TYPE: PRT
<213> ORGANISM: Artificial Sequence
<220> FEATURE:
<223> OTHER INFORMATION: synthetic polypeptide sequence

<400> SEQUENCE: 8

Leu Ser Asn Ile Asp Tyr Ile Leu Ile Lys Ala Ser
1               5                   10

<210> SEQ ID NO 9
<211> LENGTH: 5
<212> TYPE: PRT
<213> ORGANISM: Artificial Sequence
<220> FEATURE:
<223> OTHER INFORMATION: synthetic polypeptide sequence

<400> SEQUENCE: 9

Tyr Ile Gly Ser Arg
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic polypeptide sequence

<400> SEQUENCE: 10

Ile Lys Val Ala Val
1               5

<210> SEQ ID NO 11
<211> LENGTH: 4
<212> TYPE: PRT
<213> ORGANISM: Artificial Sequence
<220> FEATURE:
<223> OTHER INFORMATION: synthetic polypeptide sequence

<400> SEQUENCE: 11
```

Arg Glu Asp Val
1

<210> SEQ ID NO 12
<211> LENGTH: 4
<212> TYPE: PRT
<213> ORGANISM: Artificial Sequence
<220> FEATURE:
<223> OTHER INFORMATION: synthetic polypeptide sequence

<400> SEQUENCE: 12

Asp Gly Glu Ala
1

<210> SEQ ID NO 13
<211> LENGTH: 6
<212> TYPE: PRT
<213> ORGANISM: Artificial Sequence
<220> FEATURE:
<223> OTHER INFORMATION: synthetic polypeptide sequence

<400> SEQUENCE: 13

Val Gly Val Ala Pro Gly
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic polypeptide sequence

<400> SEQUENCE: 14

Gly Arg Gly Asp Ser
1               5

<210> SEQ ID NO 15
<211> LENGTH: 4
<212> TYPE: PRT
<213> ORGANISM: Artificial Sequence
<220> FEATURE:
<223> OTHER INFORMATION: synthetic polypeptide sequence

<400> SEQUENCE: 15

Arg Gly Asp Val
1

<210> SEQ ID NO 16
<211> LENGTH: 5
<212> TYPE: PRT
<213> ORGANISM: Artificial Sequence
<220> FEATURE:
<223> OTHER INFORMATION: synthetic polypeptide sequence

<400> SEQUENCE: 16

Pro Asp Ser Gly Arg
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic polypeptide sequence

<400> SEQUENCE: 17

Arg Tyr Val Val Leu Pro Arg
1               5

<210> SEQ ID NO 18
<211> LENGTH: 6
<212> TYPE: PRT
<213> ORGANISM: Artificial Sequence
<220> FEATURE:
<223> OTHER INFORMATION: synthetic polypeptide sequence

<400> SEQUENCE: 18

Leu Gly Thr Ile Pro Gly
1               5

<210> SEQ ID NO 19
<211> LENGTH: 4
<212> TYPE: PRT
<213> ORGANISM: Artificial Sequence
<220> FEATURE:
<223> OTHER INFORMATION: synthetic polypeptide sequence

<400> SEQUENCE: 19

Arg Gly Asp Ser
1

<210> SEQ ID NO 20
<211> LENGTH: 4
<212> TYPE: PRT
<213> ORGANISM: Artificial Sequence
<220> FEATURE:
<223> OTHER INFORMATION: synthetic polypeptide sequence

<400> SEQUENCE: 20

Arg Gly Asp Phe
1

<210> SEQ ID NO 21
<211> LENGTH: 12
<212> TYPE: PRT
<213> ORGANISM: Artificial Sequence
<220> FEATURE:
<223> OTHER INFORMATION: synthetic polypeptide sequence

<400> SEQUENCE: 21

His His Leu Gly Gly Ala Leu Gln Ala Gly Asp Val
1               5                   10

<210> SEQ ID NO 22
<211> LENGTH: 4
<212> TYPE: PRT
<213> ORGANISM: Artificial Sequence
<220> FEATURE:
<223> OTHER INFORMATION: synthetic polypeptide sequence

<400> SEQUENCE: 22

Val Thr Cys Gly
1

<210> SEQ ID NO 23
<211> LENGTH: 4
<212> TYPE: PRT
<213> ORGANISM: Artificial Sequence
<220> FEATURE:
<223> OTHER INFORMATION: synthetic polypeptide sequence

<400> SEQUENCE: 23

Ser Asp Gly Asp

```
<210> SEQ ID NO 24
<211> LENGTH: 6
<212> TYPE: PRT
<213> ORGANISM: Artificial Sequence
<220> FEATURE:
<223> OTHER INFORMATION: synthetic polypeptide sequence

<400> SEQUENCE: 24

Gly Arg Glu Asp Val Tyr
1               5

<210> SEQ ID NO 25
<211> LENGTH: 5
<212> TYPE: PRT
<213> ORGANISM: Artificial Sequence
<220> FEATURE:
<223> OTHER INFORMATION: synthetic polypeptide sequence

<400> SEQUENCE: 25

Gly Arg Gly Asp Tyr
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic polypeptide sequence

<400> SEQUENCE: 26

Gly Arg Gly Asp Ser Pro
1               5

<210> SEQ ID NO 27
<211> LENGTH: 4
<212> TYPE: PRT
<213> ORGANISM: Artificial Sequence
<220> FEATURE:
<223> OTHER INFORMATION: synthetic polypeptide sequence

<400> SEQUENCE: 27

Val Ala Pro Gly
1

<210> SEQ ID NO 28
<211> LENGTH: 9
<212> TYPE: PRT
<213> ORGANISM: Artificial Sequence
<220> FEATURE:
<223> OTHER INFORMATION: synthetic polypeptide sequence

<400> SEQUENCE: 28

Gly Gly Gly Gly Arg Gly Asp Ser Pro
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic polypeptide sequence

<400> SEQUENCE: 29

Gly Gly Gly Gly Arg Gly Asp Tyr
1               5
```

```
<210> SEQ ID NO 30
<211> LENGTH: 6
<212> TYPE: PRT
<213> ORGANISM: Artificial Sequence
<220> FEATURE:
<223> OTHER INFORMATION: synthetic polypeptide sequence

<400> SEQUENCE: 30

Phe Thr Leu Cys Phe Asp
1               5

<210> SEQ ID NO 31
<211> LENGTH: 12
<212> TYPE: PRT
<213> ORGANISM: Artificial Sequence
<220> FEATURE:
<223> OTHER INFORMATION: synthetic polypeptide sequence

<400> SEQUENCE: 31

Arg Lys Arg Leu Gln Val Gln Leu Ser Ile Arg Thr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: synthetic polypeptide sequence

<400> SEQUENCE: 32

Lys Ala Phe Asp Ile Thr Tyr Val Arg Leu Lys Phe
1               5                   10

<210> SEQ ID NO 33
<211> LENGTH: 30
<212> TYPE: PRT
<213> ORGANISM: Artificial Sequence
<220> FEATURE:
<223> OTHER INFORMATION: synthetic polypeptide sequence

<400> SEQUENCE: 33

Trp Tyr Arg Asn Cys His Arg Val Asn Leu Met Gly Arg Tyr Gly Asp
1               5                   10                  15

Asn Asn His Ser Gln Gly Val Asn Trp Phe His Trp Lys Gly
                20                  25                  30
```